United States Patent
Pizza et al.

(10) Patent No.: US 12,161,707 B2
(45) Date of Patent: Dec. 10, 2024

(54) VACCINES FOR NEISSERIA GONORRHOEAE

(71) Applicant: GLAXOSMITHKLINE BIOLOGICALS SA, Rixensart (BE)

(72) Inventors: Mariagrazia Pizza, Siena (IT); Marzia Monica Giuliani, Siena (IT); Elisabetta Monaci, Siena (IT)

(*) Notice: Subject to any disclaimer, the term of this patent is extended or adjusted under 35 U.S.C. 154(b) by 273 days.

(21) Appl. No.: 15/693,663

(22) Filed: Sep. 1, 2017

(65) Prior Publication Data
US 2018/0064801 A1 Mar. 8, 2018

Related U.S. Application Data

(60) Provisional application No. 62/383,134, filed on Sep. 2, 2016.

(51) Int. Cl.
| | | |
|---|---|---|
| A61K 39/095 | (2006.01) | |
| A61K 39/116 | (2006.01) | |
| A61K 39/39 | (2006.01) | |
| A61K 47/64 | (2017.01) | |
| C07K 14/22 | (2006.01) | |
| C07K 16/12 | (2006.01) | |
| A61K 39/00 | (2006.01) | |

(52) U.S. Cl.
CPC .......... *A61K 39/095* (2013.01); *A61K 39/116* (2013.01); *A61K 39/39* (2013.01); *A61K 47/646* (2017.08); *C07K 14/22* (2013.01); *C07K 16/1217* (2013.01); *A61K 2039/54* (2013.01); *A61K 2039/55* (2013.01); *A61K 2039/55505* (2013.01); *A61K 2039/58* (2013.01); *C07K 2317/33* (2013.01)

(58) Field of Classification Search
None
See application file for complete search history.

(56) References Cited

U.S. PATENT DOCUMENTS

| | | | |
|---|---|---|---|
| 4,186,182 A | 1/1980 | Gaafar et al. | |
| 9,259,462 B2* | 2/2016 | Serruto | A61K 39/095 |
| 9,764,027 B2 | 9/2017 | Grandi et al. | |
| 10,179,167 B2* | 1/2019 | Serruto | A61K 39/095 |
| 10,376,573 B2* | 8/2019 | Pizza | A61K 39/095 |
| 2005/0222385 A1 | 10/2005 | Pizza | |
| 2008/0063665 A1 | 3/2008 | Oster et al. | |
| 2013/0022639 A1 | 1/2013 | Oriente et al. | |
| 2013/0236489 A1* | 9/2013 | Serruto | A61K 39/095 |
| | | | 424/190.1 |
| 2015/0291666 A1* | 10/2015 | Jerse | A61P 31/04 |
| | | | 424/139.1 |
| 2016/0166674 A1* | 6/2016 | Pizza | A61K 39/095 |
| | | | 424/190.1 |
| 2019/0282684 A1 | 9/2019 | Pizza et al. | |

FOREIGN PATENT DOCUMENTS

| | | |
|---|---|---|
| EP | 1977761 A2 | 10/2008 |
| JP | 2003-518363 A | 6/2003 |
| JP | 2007-508537 A | 4/2007 |
| JP | 2013-521770 A | 6/2013 |
| WO | 2000066741 A2 | 11/2000 |
| WO | 2005/032583 A2 | 4/2005 |
| WO | 2005/035733 A | 4/2005 |
| WO | 2011110634 A1 | 9/2011 |
| WO | 2018042015 A1 | 3/2018 |
| WO | 2018042017 A2 | 3/2018 |

OTHER PUBLICATIONS

McGuinnes et al. Lancet 337: 514-517, 1991.*
McGuinnes et al. Mol. Microbiol. 7: 505-514, 1993.*
Skolnick et al. Trends in Biotechnology 18: 34-39, 2000.*
Thomson Reuters ONE, pp. 1-3, Feb. 24, 2014.*
Pogany et al. Can. Fam. Physician 61: 869-873, 2015.*
Read et al. Lancet 384: 2123-2131, 2014.*
Morbidity and Mortality Weekly Report (Mmwr), CDC 64 (22): 608-612, pp. 1/7 to 7/7, Jun. 12, 2015.*
O'Ryan et al. Drugs 74: 15-30, 2014.*
Kidd et al. Clin. Infect. Dis. 61: Suppl. 8: S785-S801, available in PMC Sep. 18, 2015.*
Moore EW . J. Amer. College Hlth 61: 196-202, 2013.*
Santolaya et al. Hum. Vaccin. Immunother. 9:11, 2304-2310, 2013.*
Knighting et al. Health Serv. Deliv. Res. 9: 1-268, 2021.*
Toneatto et al. Hum. Vaccin. 7: 646-653, 2011.*
Chen, et al., "Adherence of pilus-Opa+gonococci to epithelial cells in vitro involves heparin sulfate", The Journal of Experimental Medicine, vol. 182, No. 2, Aug. 1995.
Cuello et al., "Nasal immunization with AFCol induces immune response to N. gonorrhoea in mice", VacciMonitor, Aug. 2009, pp. 76-78.
Li et al., "Neisseria gonorrhoeae NspA Induces Specific Bactericidal and Opsonic Antibodies in Mice", Clinical and Vaccine Immunology, vol. 18, No. 11, Nov. 2011, pp. 1817-1822.
Perez et al., "Heterologous Prime-Boost Immunization with VA-Mengoc-BC and AFCo1 Elicits Systemic and Mucosal Immunity to Neisseria meningitides and N gonorrhoeae", Revista VacciMonitor, Jan. 2010, pp. 1-2.
Perez, et al., "Netural Neissera Derive Proteoliposome and Cochleate as Potent Vaccine Adjuvants", Pharmacologyonline, Jan. 2006, pp. 762-764. Plante et al., "Intranasal Immunization with Gonococcal Outer Membrane Preparations Reduces the Duration of Vaginal Colonization of Mice by Neisseria gonorrhoeae", The Journal of Infectious Diseases, Sep. 2000, pp. 848-855.
Price et al., "Intranasal Administration of Recombinant Neisseria gonorrhoeae Transferrin Binding Proteins A and B Conjugated to the Cholera Toxin B Subunit Induces Systemic and Vaginal Antibodies in Mice", Infection and Immunity, vol. 73, No. 7, Jul. 2005, pp. 3945-3953.
Rippa et al., "Molecular Engineering of Ghfp, the Gonococcal Orthologue of Neisseria meningitides Factor H Binding Protein", Clinical and Vaccine Immunology, vol. 22, No. 7, May 6, 2015, pp. 769-777.

(Continued)

*Primary Examiner* — S. Devi

(57) ABSTRACT

Methods and compositions for immunizing a human subject against *Neisseria gonorrhoeae*.

10 Claims, 22 Drawing Sheets
Specification includes a Sequence Listing.

(56) References Cited

OTHER PUBLICATIONS

Seib et al., "Characterization of Diverse Subvariants of the Meningococcal Factor H (fH) Binding Protein for their Ability to Bind fH, to Mediate Serum Resistance, and to Induce Bactericidal Antibodies", Infection and Immunity, vol. 79, No. 2, Feb. 2011, pp. 970-981.
Whelan et al., "Ecologic Study of Meningococcal B Vaccine and Neisseria gonorrhoeae Infection, Norway", Emerging Infectious Diseases, vol. 22, No. 6, Nov. 16, 2011, pp. 1137-1139.
Zhu et al., "Comparison of Immune Responses to Gonococcal PorB Delivered as Outer Membrane Vesicles, Recombinant Protein, or Venezuelan Equine Encephalitis Virus Replicon Particles", Infection and Immunity, vol. 73, No. 11, Nov. 2005, pp. 7558-7568.
Muzzi et al., "Conservation of Meningococcal Antigens in the Genus *Neisseria*", mBIO, vol. 4, No. 3, Jun. 2013, pp. e00163-13.
Acevedo et al., "Bacterial outer membrane vesicles and vaccine applications.", Front Immunol., vol. 5, No. 121, Mar. 24, 2014, pp. 1-6.
Perez et al., "Mucosal approaches in Neisseria Vaccinology", VacciMonitor, vol. 18, No. 2, 2009, pp. 53-55.
Cremieux et al., "Bactericidal Antibodies Against Neisseria Gonorrhoeae Elicited by Neisseria Meningitidis", Lancet, vol. 324, No. 8408, 1984, p. 930.
Petousis-Harris, Abstract 1A3 entitled "Effectiveness of a Group B OMV Meningococcal Vaccine on Gonorrhoea in New Zealand—a Case Control Study" for the 2016 STD Prevention Conference, Sep. 21, 2016, 1 Pg.
Gokhale, "Struggling Vaccines From Novartis Turn Into Sales Boon for Glaxo", Aug. 31, 2016 article in Bloomberg Business; available at https://www.bloomberg.com/news/articles/2016-08-31/struggling-vaccines-from-novartis-turn-into-sales-boon-for-glaxo; last visited May 21, 2019; 3 pages.
Liu et al., "Experimental vaccine induces Th1-driven immune responses and resistance to Neisseria gonorrhoeae infection in a murine model", Mucosal Immunology, vol. 10, No. 6; Mar. 1, 2017; pp. 1594-1608.
Panatto et al., The Indian Journal of Medical Research Dec. 2013; 138(6): 835-846.
Perera et al: "The role of pili and outer membrane vesicles in the immunogenicity of Neisseria gonorrhoeae in the guinea pig chamber model", FEMS Microbiology Letters, Wiley-Blackwell Publishing Ltd, GB, vol. 17, No. 1-3, Mar. 1, 1983, (Mar. 1, 1983), pp. 303-306.
Regnier, et al., "Potential impact of vaccination against Neisseria meningitidis on Neisseria gonorrhoeae in the United States: Results from a decision-analysis model", Human Vaccines and Immunotherpeutics, vol. 10, No. 12, Nov. 1, 2014 (Nov. 1, 2014), pp. 3737-3745.

Semchenko et al., "Neisseria heparin binding antigen (NHBA): A potential vaccine candidate for Meisseria gonorrhoeae", Jan. 1, 2015; p. 1.
Todar, Kenneth "Pathogenic Neisseriae: Gonorrhoea, Neonatal Ophthalmia and Meningococcal Meningitis" in Todar's Online Textbook of Bacteriology 2008, 13 pages, available at http://www.textbookofbacteriology.net/neisseria_1.html.
Dehne et al. Sexually Transmitted Infections Among Adolescents The Need for Adequate Health Services. World Health Organization 2005. 93 pages.
Mameli et al. Future Microbial. (2015) 10(10), 1579-1598.
Santolaya et al. Lancet 2012; 379:617-24.
Gokhale, Business "Struggling Vaccines from Novartis turn into Sales Boon for Glaxo" Aug. 31, 2016.
Hadad, et al., "Novel Meningococcal 4CMenB vaccine antigens—prevalence and polymorphisms of the encoding genes in Neisseria gonorrhoeae", APMIS (2012) 120: 750-760.
Evaluation of Meningococcal B Immunisation National Roll-out Final Report CBG Health Research Nov. 2006 retrieved Nov. 7, 2022 from https://www.health.govt.nz/system/files/documents/publications/menzb-implementation-evaluation-nov06.pdf).
BacPath 13: Molecular Analysis of Bacterial Pathogens Conference, Poster Presentation (2015), 1 page.
Hadad, et al., "Novel Meningococcal 4CMenB vaccine antigens—prevalence and polymorphisms of the encoding genes in Neisseria gonorrhoeae", APMIS (2012) 120: 750-760.
Knighting et al., Health Serv. Deliv. Res (2021) 9.6 (7 pages).
Oster et al. Vaccine 23 (2005) 2191-2196.
Petousis-Harris, et al., Lancet, 2017, 390; 1603-1610.
Semchenko et al., Clinical Infectious Diseases, 69(7): 1101-1111, 2019.
Valenzuela, et al., Vaccine 2005, 23(32), pp. 4110-4119.
Meningococcal B Immunisation Evaluation Final Report CBG Health Research Nov. 2006 retrieved Nov. 7, 2022 from https://www.health.govt.nz/system/files/documents/publications/menzb-implementation-evaluation-nov06.pdf.
GBD 2015 Disease and Injury Incidence and Prevalence Collaborators, "Global, regional, and national incidence, prevalence, and years lived with disability for 310 diseases and injuries, 1990-2015: a systematic analysis for the Global Burden of Disease Study 2015." Lancet (2016) 388:1545-602.
European Patent Office as International Searching Authority, International Search Report and Written Opinion for corresponding International Application PCT/EP2017/072011, mailed Mar. 21, 2018 (27 pages).
European Patent Office as International Searching Authority, International Search Report and Written Opinion for corresponding International Application PCT/EP2017/072009, mailed Nov. 3, 2017 (14 pages).

\* cited by examiner

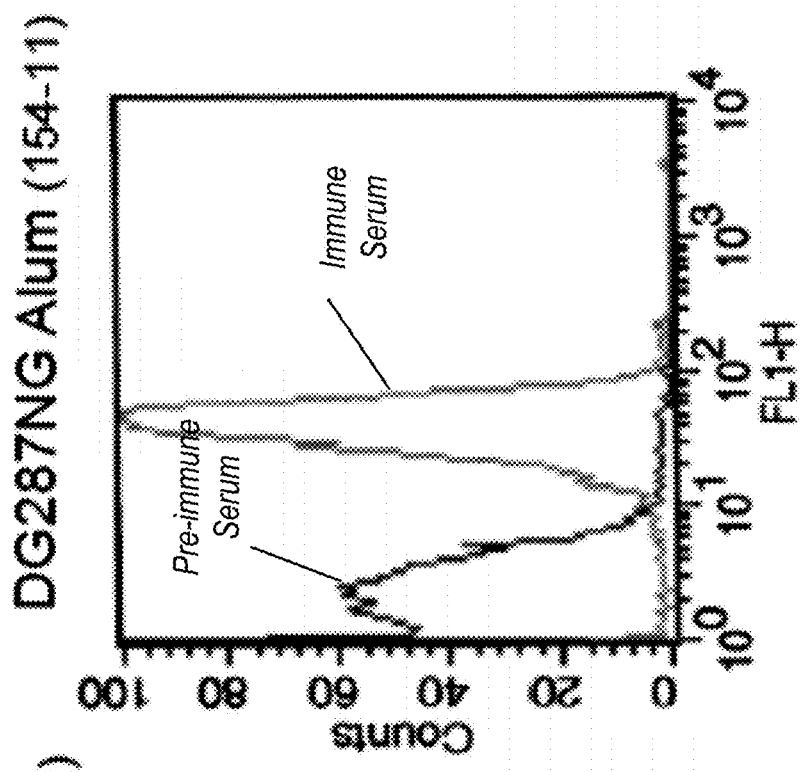
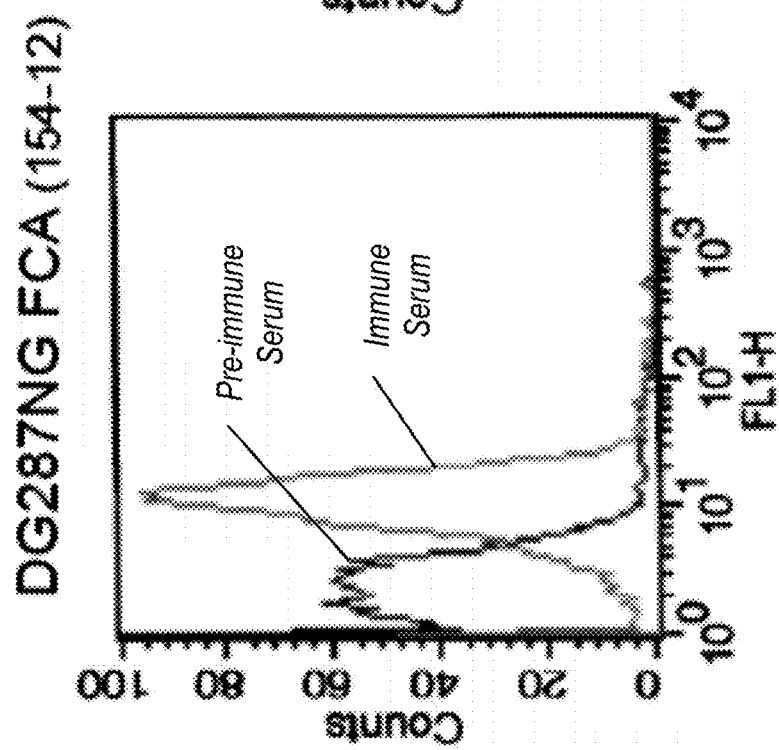
Fig. 1A
Fig. 1B

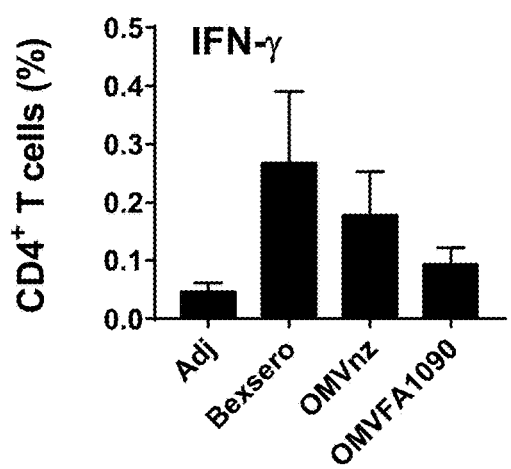
Fig. 18A Th1
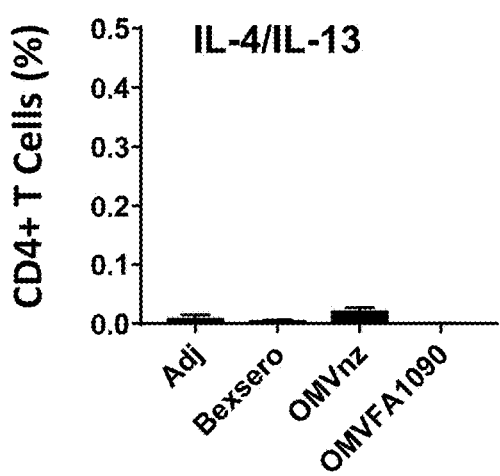
Fig. 18B Th2
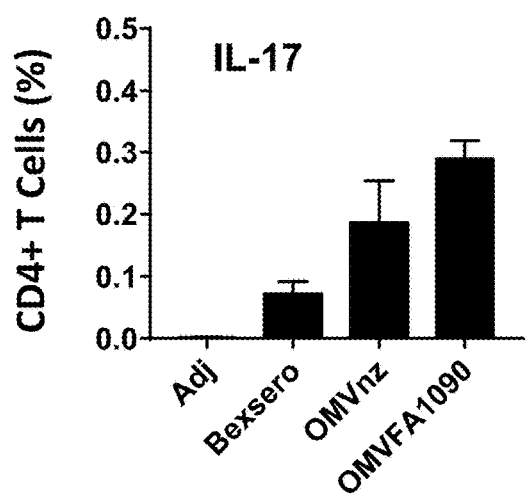
Fig. 18C Th17
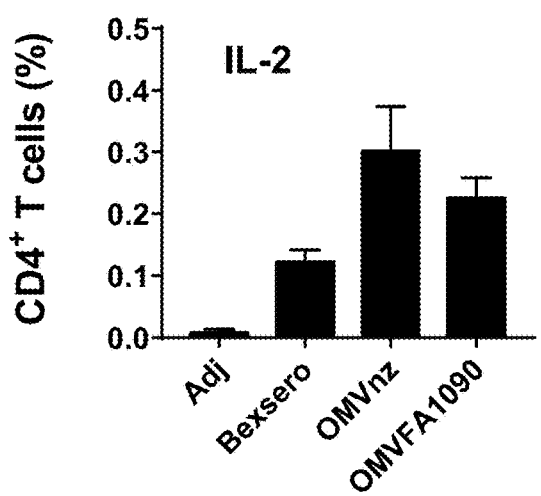
Fig. 18D Th0

SEQUENCE LISTING

<160> NUMBER OF SEQ ID NOS: 15

<210> SEQ ID NO 1
<211> LENGTH: 255
<212> TYPE: PRT
<213> ORGANISM: Neisseria meningitidis

<400> SEQUENCE: 1

Cys Ser Ser Gly Gly Gly Gly Val Ala Ala Asp Ile Gly Ala Gly Leu
1               5                   10                  15

```
Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 2
<211> LENGTH: 254
<212> TYPE: PRT
<213> ORGANISM: Neisseria meningitidis

<400> SEQUENCE: 2

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
```

```
                130             135             140
Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
                195                 200                 205

Gly Asp Thr Arg Tyr Gly Ser Glu Glu Lys Gly Thr Tyr His Leu Ala
            210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 3
<211> LENGTH: 262
<212> TYPE: PRT
<213> ORGANISM: Neisseria meningitidis

<400> SEQUENCE: 3

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
        50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
                100                 105                 110

Ala Val Val Ala Leu Gln Ile Glu Lys Ile Asn Asn Pro Asp Lys Thr
            115                 120                 125

Asp Ser Leu Ile Asn Gln Arg Ser Phe Leu Val Ser Gly Leu Gly Gly
        130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
                180                 185                 190

Thr Leu Glu Gln Asn Val Glu Leu Ala Ala Ala Glu Leu Lys Ala Asp
            195                 200                 205

Glu Lys Ser His Ala Val Ile Leu Gly Asp Thr Arg Tyr Gly Ser Glu
        210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255
```

```
Gly Ile Ala Gly Lys Gln
            260

<210> SEQ ID NO 4
<211> LENGTH: 488
<212> TYPE: PRT
<213> ORGANISM: Neisseria meningitidis

<400> SEQUENCE: 4

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
            35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
            115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
            195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
            275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
            355                 360                 365
```

```
Ala Lys Gly Glu Met Leu Ala Gly Ala Ala Val Tyr Asn Gly Glu Val
    370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
    450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 5
<211> LENGTH: 364
<212> TYPE: PRT
<213> ORGANISM: Neisseria meningitidis

<400> SEQUENCE: 5

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
                20                  25                  30

Lys Lys Ala Ala Thr Val Ala Ile Val Ala Ala Tyr Asn Asn Gly Gln
            35                  40                  45

Glu Ile Asn Gly Phe Lys Ala Gly Glu Thr Ile Tyr Asp Ile Gly Glu
        50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
                100                 105                 110

Ala Glu Ser Glu Ile Glu Lys Leu Thr Thr Lys Leu Ala Asp Thr Asp
            115                 120                 125

Ala Ala Leu Ala Asp Thr Asp Ala Ala Leu Asp Glu Thr Thr Asn Ala
        130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
                180                 185                 190

Glu Thr Asn Thr Lys Ala Asp Glu Ala Val Lys Thr Ala Asn Glu Ala
            195                 200                 205

Lys Gln Thr Ala Glu Glu Thr Lys Gln Asn Val Asp Ala Lys Val Lys
        210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Ala Lys Val Thr Asp
```

```
                        245                 250                 255
Ile Lys Ala Asp Ile Ala Thr Asn Lys Ala Asp Ile Ala Lys Asn Ser
                260                 265                 270

Ala Arg Ile Asp Ser Leu Asp Lys Asn Val Ala Asn Leu Arg Lys Glu
                275                 280                 285

Thr Arg Gln Gly Leu Ala Glu Gln Ala Ala Leu Ser Gly Leu Phe Gln
                290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
                340                 345                 350

Ser Ala Ala Tyr His Val Gly Val Asn Tyr Glu Trp
                355                 360

<210> SEQ ID NO 6
<211> LENGTH: 248
<212> TYPE: PRT
<213> ORGANISM: Neisseria meningitidis

<400> SEQUENCE: 6

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
                35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
                180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245
```

```
<210> SEQ ID NO 7
<211> LENGTH: 434
<212> TYPE: PRT
<213> ORGANISM: Artificial Sequence
<220> FEATURE:
<223> OTHER INFORMATION: Fusion protein of fHbp

<400> SEQUENCE: 7

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asp Arg His
    50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Arg Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
    290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
        355                 360                 365
```

Asn Val Asp Leu Ala Ala Ala Asp Ile Lys Pro Asp Gly Lys Arg His
    370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
                420                 425                 430

Lys Gln

<210> SEQ ID NO 8
<211> LENGTH: 468
<212> TYPE: PRT
<213> ORGANISM: Neisseria meningitidis

<400> SEQUENCE: 8

Ser Pro Asp Val Lys Ser Ala Asp Thr Leu Ser Lys Pro Ala Ala Pro
1               5                   10                  15

Val Val Ser Glu Lys Glu Thr Glu Ala Lys Glu Asp Ala Pro Gln Ala
                20                  25                  30

Gly Ser Gln Gly Gln Gly Ala Pro Ser Ala Gln Gly Gly Gln Asp Met
            35                  40                  45

Ala Ala Val Ser Glu Glu Asn Thr Gly Asn Gly Gly Ala Ala Ala Thr
50                  55                  60

Asp Lys Pro Lys Asn Glu Asp Glu Gly Ala Gln Asn Asp Met Pro Gln
65                  70                  75                  80

Asn Ala Ala Asp Thr Asp Ser Leu Thr Pro Asn His Thr Pro Ala Ser
                85                  90                  95

Asn Met Pro Ala Gly Asn Met Glu Asn Gln Ala Pro Asp Ala Gly Glu
            100                 105                 110

Ser Glu Gln Pro Ala Asn Gln Pro Asp Met Ala Asn Thr Ala Asp Gly
            115                 120                 125

Met Gln Gly Asp Asp Pro Ser Ala Gly Gly Glu Asn Ala Gly Asn Thr
130                 135                 140

Ala Ala Gln Gly Thr Asn Gln Ala Glu Asn Asn Gln Thr Ala Gly Ser
145                 150                 155                 160

Gln Asn Pro Ala Ser Ser Thr Asn Pro Ser Ala Thr Asn Ser Gly Gly
                165                 170                 175

Asp Phe Gly Arg Thr Asn Val Gly Asn Ser Val Val Ile Asp Gly Pro
            180                 185                 190

Ser Gln Asn Ile Thr Leu Thr His Cys Lys Gly Asp Ser Cys Ser Gly
            195                 200                 205

Asn Asn Phe Leu Asp Glu Glu Val Gln Leu Lys Ser Glu Phe Glu Lys
210                 215                 220

Leu Ser Asp Ala Asp Lys Ile Ser Asn Tyr Lys Lys Asp Gly Lys Asn
225                 230                 235                 240

Asp Gly Lys Asn Asp Lys Phe Val Gly Leu Val Ala Asp Ser Val Gln
                245                 250                 255

Met Lys Gly Ile Asn Gln Tyr Ile Ile Phe Tyr Lys Pro Lys Pro Thr
            260                 265                 270

Ser Phe Ala Arg Phe Arg Arg Ser Ala Arg Ser Arg Ser Leu Pro
            275                 280                 285

Ala Glu Met Pro Leu Ile Pro Val Asn Gln Ala Asp Thr Leu Ile Val
            290                 295                 300

-continued

```
Asp Gly Glu Ala Val Ser Leu Thr Gly His Ser Gly Asn Ile Phe Ala
305                 310                 315                 320

Pro Glu Gly Asn Tyr Arg Tyr Leu Thr Tyr Gly Ala Glu Lys Leu Pro
            325                 330                 335

Gly Gly Ser Tyr Ala Leu Arg Val Gln Gly Glu Pro Ser Lys Gly Glu
            340                 345                 350

Met Leu Ala Gly Thr Ala Val Tyr Asn Gly Glu Val Leu His Phe His
            355                 360                 365

Thr Glu Asn Gly Arg Pro Ser Pro Ser Arg Gly Arg Phe Ala Ala Lys
            370                 375                 380

Val Asp Phe Gly Ser Lys Ser Val Asp Gly Ile Ile Asp Ser Gly Asp
385                 390                 395                 400

Gly Leu His Met Gly Thr Gln Lys Phe Lys Ala Ala Ile Asp Gly Asn
            405                 410                 415

Gly Phe Lys Gly Thr Trp Thr Glu Asn Gly Gly Asp Val Ser Gly
            420                 425                 430

Lys Phe Tyr Gly Pro Ala Gly Glu Glu Val Ala Gly Lys Tyr Ser Tyr
            435                 440                 445

Arg Pro Thr Asp Ala Glu Lys Gly Gly Phe Gly Val Phe Ala Gly Lys
450                 455                 460

Lys Glu Gln Asp
465

<210> SEQ ID NO 9
<211> LENGTH: 644
<212> TYPE: PRT
<213> ORGANISM: Artificial Sequence
<220> FEATURE:
<223> OTHER INFORMATION: Fusion protein of NHBA

<400> SEQUENCE: 9

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
            35                  40                  45

Asp Met Ala Ala Val Ser Glu Glu Asn Thr Gly Asn Gly Gly Ala Ala
        50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
            85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
            115                 120                 125

Asp Gly Met Gln Gly Asp Asp Pro Ser Ala Gly Gly Glu Asn Ala Gly
        130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
            165                 170                 175

Gly Gly Asp Phe Gly Arg Thr Asn Val Gly Asn Ser Val Ile Asp
            180                 185                 190
```

```
Gly Pro Ser Gln Asn Ile Thr Leu Thr His Cys Lys Gly Asp Ser Cys
            195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
    530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
```

```
                610               615               620
Val Asn Val Gly Met Thr Lys Ser Val Arg Ile Asp Ile Gln Ile Glu
625               630               635               640

Ala Ala Lys Gln

<210> SEQ ID NO 10
<211> LENGTH: 327
<212> TYPE: PRT
<213> ORGANISM: Neisseria meningitidis

<400> SEQUENCE: 10

Ala Thr Asn Asp Asp Val Lys Lys Ala Thr Val Ala Ile Ala
1               5                   10                  15

Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
            35                  40                  45

Thr Ala Ala Asp Val Glu Ala Asp Asp Phe Lys Gly Leu Gly Leu Lys
        50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
        275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325
```

<210> SEQ ID NO 11
<211> LENGTH: 261
<212> TYPE: PRT
<213> ORGANISM: Neisseria meningitidis

<400> SEQUENCE: 11

```
Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Phe Lys Val Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Ser Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260
```

<210> SEQ ID NO 12
<211> LENGTH: 260
<212> TYPE: PRT
<213> ORGANISM: Neisseria meningitidis

<400> SEQUENCE: 12

```
Cys Ser Ser Gly Gly Gly Ser Gly Gly Gly Val Thr Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
```

```
                65                  70                  75                  80
        Phe Asp Phe Ile Arg Gln Ile Glu Val Asp Gly Gln Leu Ile Thr Leu
                        85                  90                  95

Glu Ser Gly Glu Phe Gln Val Tyr Lys Gln Ser His Ser Ala Leu Thr
                    100                 105                 110

Ala Leu Gln Thr Glu Gln Gln Asp Pro Glu His Ser Glu Lys Met
                115                 120                 125

Val Ala Lys Arg Arg Phe Arg Ile Gly Asp Ile Ala Gly Glu His Thr
            130                 135                 140

Ser Phe Asp Lys Leu Pro Lys Asp Val Met Ala Thr Tyr Arg Gly Thr
        145                 150                 155                 160

Ala Phe Gly Ser Asp Asp Ala Gly Gly Lys Leu Thr Tyr Thr Ile Asp
                        165                 170                 175

Phe Ala Ala Lys Gln Gly His Gly Lys Ile Glu His Leu Lys Ser Pro
                    180                 185                 190

Glu Leu Asn Val Asp Leu Ala Val Ala Tyr Ile Lys Pro Asp Glu Lys
                195                 200                 205

His His Ala Val Ile Ser Gly Ser Val Leu Tyr Asn Gln Asp Glu Lys
            210                 215                 220

Gly Ser Tyr Ser Leu Gly Ile Phe Gly Glu Lys Ala Gln Glu Val Ala
        225                 230                 235                 240

Gly Ser Ala Glu Val Glu Thr Ala Asn Gly Ile His His Ile Gly Leu
                        245                 250                 255

Ala Ala Lys Gln
                    260

<210> SEQ ID NO 13
<211> LENGTH: 168
<212> TYPE: PRT
<213> ORGANISM: Neisseria meningitidis

<400> SEQUENCE: 13

Ala Thr Tyr Lys Val Asp Glu Tyr His Ala Asn Ala Arg Phe Ala Ile
        1               5                   10                  15

Asp His Phe Asn Thr Ser Thr Asn Val Gly Gly Phe Tyr Gly Leu Thr
                        20                  25                  30

Gly Ser Val Glu Phe Asp Gln Ala Lys Arg Asp Gly Lys Ile Asp Ile
                    35                  40                  45

Thr Ile Pro Ile Ala Asn Leu Gln Ser Gly Ser Gln His Phe Thr Asp
                50                  55                  60

His Leu Lys Ser Ala Asp Ile Phe Asp Ala Ala Gln Tyr Pro Asp Ile
        65                  70                  75                  80

Arg Phe Val Ser Thr Lys Phe Asn Phe Asn Gly Lys Lys Leu Val Ser
                        85                  90                  95

Val Asp Gly Asn Leu Thr Met His Gly Lys Thr Ala Pro Val Lys Leu
                    100                 105                 110

Lys Ala Glu Lys Phe Asn Cys Tyr Gln Ser Pro Met Glu Lys Thr Glu
                115                 120                 125

Val Cys Gly Gly Asp Phe Ser Thr Thr Ile Asp Arg Thr Lys Trp Gly
            130                 135                 140

Met Asp Tyr Leu Val Asn Val Gly Met Thr Lys Ser Val Arg Ile Asp
        145                 150                 155                 160

Ile Gln Ile Glu Ala Ala Lys Gln
                        165
```

```
<210> SEQ ID NO 14
<211> LENGTH: 179
<212> TYPE: PRT
<213> ORGANISM: Neisseria meningitidis

<400> SEQUENCE: 14

Val Ser Ala Val Ile Gly Ser Ala Ala Val Gly Ala Lys Ser Ala Val
1               5                   10                  15

Asp Arg Arg Thr Thr Gly Ala Gln Thr Asp Asp Asn Val Met Ala Leu
            20                  25                  30

Arg Ile Glu Thr Thr Ala Arg Ser Tyr Leu Arg Gln Asn Asn Gln Thr
        35                  40                  45

Lys Gly Tyr Thr Pro Gln Ile Ser Val Val Gly Tyr Asn Arg His Leu
    50                  55                  60

Leu Leu Leu Gly Gln Val Ala Thr Glu Gly Lys Gln Phe Val Gly
65                  70                  75                  80

Gln Ile Ala Arg Ser Glu Gln Ala Ala Glu Gly Val Tyr Asn Tyr Ile
                85                  90                  95

Thr Val Ala Ser Leu Pro Arg Thr Ala Gly Asp Ile Ala Gly Asp Thr
            100                 105                 110

Trp Asn Thr Ser Lys Val Arg Ala Thr Leu Leu Gly Ile Ser Pro Ala
        115                 120                 125

Thr Gln Ala Arg Val Lys Ile Val Thr Tyr Gly Asn Val Thr Tyr Val
    130                 135                 140

Met Gly Ile Leu Thr Pro Glu Glu Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg

<210> SEQ ID NO 15
<211> LENGTH: 405
<212> TYPE: PRT
<213> ORGANISM: Neisseria gonorrhoeae

<400> SEQUENCE: 15

Ser Pro Asp Val Lys Ser Ala Asp Thr Pro Ser Lys Pro Ala Ala Pro
1               5                   10                  15

Val Val Ala Glu Asn Ala Gly Glu Gly Val Leu Pro Lys Glu Lys Lys
            20                  25                  30

Asp Glu Glu Ala Ala Gly Gly Ala Pro Gln Ala Asp Thr Gln Asp Ala
        35                  40                  45

Thr Ala Gly Glu Gly Ser Gln Asp Met Ala Ala Val Ser Ala Glu Asn
    50                  55                  60

Thr Gly Asn Gly Gly Ala Ala Thr Thr Asp Asn Pro Lys Asn Glu Asp
65                  70                  75                  80

Ala Gly Ala Gln Asn Asp Met Pro Gln Asn Ala Ala Glu Ser Ala Asn
                85                  90                  95

Gln Thr Gly Asn Asn Gln Pro Ala Gly Ser Ser Asp Ser Ala Pro Ala
            100                 105                 110

Ser Asn Pro Ala Pro Ala Asn Gly Gly Ser Asp Phe Gly Arg Thr Asn
        115                 120                 125

Val Gly Asn Ser Val Val Ile Asp Gly Pro Ser Gln Asn Ile Thr Leu
    130                 135                 140

Thr His Cys Lys Gly Asp Ser Cys Asn Gly Asp Asn Leu Leu Asp Glu
```

```
145                 150                 155                 160
Glu Ala Pro Ser Lys Ser Glu Phe Glu Lys Leu Ser Asp Glu Glu Lys
                165                 170                 175

Ile Lys Arg Tyr Lys Lys Asp Glu Gln Arg Glu Asn Phe Val Gly Leu
                180                 185                 190

Val Ala Asp Arg Val Lys Lys Asp Gly Thr Asn Lys Tyr Ile Ile Phe
                195                 200                 205

Tyr Thr Asp Lys Pro Pro Thr Arg Ser Ala Arg Ser Arg Arg Ser Leu
            210                 215                 220

Pro Ala Glu Ile Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
                260                 265                 270

Pro Gly Gly Ser Tyr Ala Leu Arg Val Gln Gly Glu Pro Ala Lys Gly
                275                 280                 285

Glu Met Leu Val Gly Thr Ala Val Tyr Asn Gly Glu Val Leu His Phe
            290                 295                 300

His Met Glu Asn Gly Arg Pro Tyr Pro Ser Gly Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
                340                 345                 350

Asn Gly Phe Lys Gly Thr Trp Thr Glu Asn Gly Gly Gly Asp Val Ser
                355                 360                 365

Gly Arg Phe Tyr Gly Pro Ala Gly Glu Glu Val Ala Gly Lys Tyr Ser
            370                 375                 380

Tyr Arg Pro Thr Asp Ala Glu Lys Gly Gly Phe Gly Val Phe Ala Gly
385                 390                 395                 400

Lys Lys Asp Arg Asp
            405
```

VACCINES FOR *NEISSERIA GONORRHOEAE*

TECHNICAL FIELD

This invention is in the field of vaccines for immunizing against *Neisseria gonorrhoeae*.

BACKGROUND

*Neisseria gonorrhoeae* and *Neisseria meningitidis* are Gram-negative bacterial pathogens. *N. gonorrhoeae* is the causative agent of gonorrhoea, whereas *N. meningitidis* causes meningitis and septicaemia.

Gonorrhoea is a major global public health concern exacerbated by multiple drug-resistance, with an estimated 78 million incident new cases each year [1]. Antimicrobial resistance of gonococci has grown steadily since the 1940s with the emergence of extensively drug-resistant strains [2,3]. Natural infection with gonorrhoea does not induce protective immunity, with repeated infection common [4]. The increase of antibiotic-resistant and untreatable gonococcal strains emphasizes the need to develop an effective vaccine.

Efforts to develop an effective vaccine against gonorrhoea have been unsuccessful despite over a century of research [5]. Challenges include the absence of a correlate of protection, lack of a suitable laboratory animal model, subversion of the immune response by the gonococcus to favour survival, and high antigenic variability. The four vaccine candidates to reach clinical trials have been whole cell, pilin and Protein 1 vaccines, but none was effective [5, 6,7]. Thus there remains a need for a vaccine which would be effective against *N. gonorrhoeae*.

Reasons for the lack of progress on vaccines for gonorrhoea include a lack of a correlate of protection, lack of a suitable laboratory model and a highly antigenically variable surface. The only trials have been the aforementioned whole cell and pilin vaccines. As recovery from infection does not confer immunity against reinfection there are unlikely to be answers from the process of natural course of infection.

While *N. gonorrhoeae* interacts with innate immune cells such as macrophage and dendritic cells and elicits inflammatory response, it suppresses the Th1/Th2 mediated specific immune responses, although a localized non-specific antibody response with no memory generated occurs [8].

One further challenge in eliciting protective immunity against *N gonorrhoeae* is the fact that gonococcal disease is generally confined to the mucosal surface.

No link between vaccination with a meningococcal vaccine and protection against gonorrhoea has been confirmed to date, and the antigens found in meningococcal vaccines have generally been considered unsuitable for immunisation against *N. gonorrhoeae* [8].

SUMMARY OF THE INVENTION

A first aspect of the invention provides a method for immunizing a human subject in need thereof against *Neisseria gonorrhoeae* by administering an immunogenic composition comprising one or more of the following protein antigens: (i) a neisserial Heparin Binding Antigen (NHBA): (ii) a neisserial factor H binding protein (fHbp) antigen; (iii) a neisserial Adhesin A (NadA) antigen; (iv) a neisserial GNA1030 antigen; (v) a neisserial GNA2091 antigen. The composition may further comprise a conjugated capsular saccharide from one or more of meningococcal serogroups A, C, W135 and/or Y.

A second aspect of the invention provides an immunogenic composition for use in immunizing a human subject in need thereof against *Neisseria gonorrhoeae*, wherein the immunogenic composition comprises one or more of the following protein antigens: (i) a NHBA antigen; (ii) a neisserial fHbp antigen; (iii) a NadA antigen; (iv) a neisserial GNA1030 antigen; (v) a neisserial GNA2091 antigen, where at least one of the antigens is a gonococcal antigen and at least one is a meningococcal antigen. The immunogenic composition may further comprise a conjugated capsular saccharide from one or more of meningococcal serogroups A, C, W135 and/or Y.

A third aspect of the invention provides an immunogenic composition comprising gonococcal Outer Membrane Vesicles (OMVs) and an adjuvant.

A fourth aspect of the invention provides a method for immunizing a human subject in need thereof against *Neisseria gonorrhoeae* by administering an immunogenic composition comprising gonococcal OMVs and an adjuvant.

BRIEF DESCRIPTION OF DRAWINGS

FIGS. 1A and 1B—Sera raised against *N. gonorrhoeae* AG287NG antigen with FCA adjuvant (A) or Alum adjuvant (B) recognize *N. gonorrhoeae* F62 strain.

FIG. 3B, antisera raised using Alum adjuvant) and mediate complement deposition (FIG. 3C, antisera raised using FCA adjuvant; FIG. 3D, antisera raised using Alum adjuvan).

FIG. 12B presents individual hSBA results for 936-741, with each dot representing the serum assay from a single mouse.

FIG. 18A-18E—Graphs showing that BEXSERO® induces cytokines indicating a T-cell response with a Th1 profile, where FIG. 18A graphs IFN-γ production; FIG. 18B graphs IL-4 and IL-13; FIG. 18C graphs IL-17; FIG. 18D graphs IL-2; and FIG. 18E graphs TNF.

DETAILED DISCLOSURE

Figure 2B:
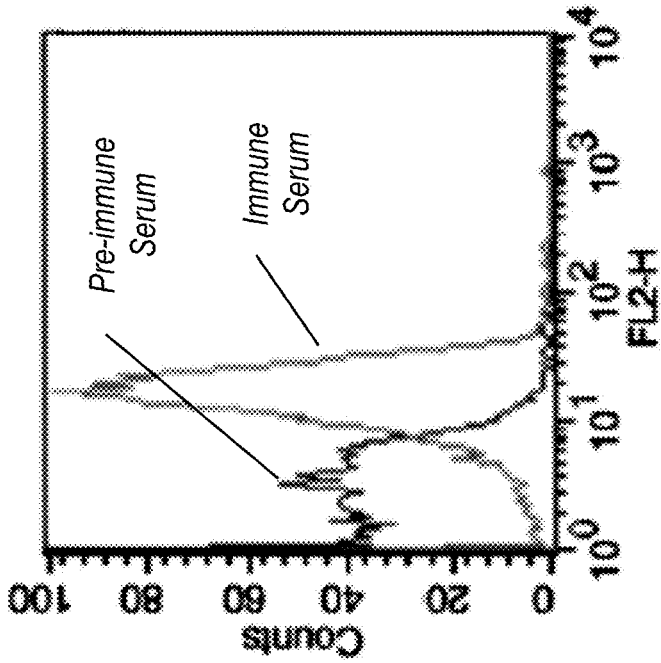
FIG. 2A-2D—Antibodies raised against *N. meningitidis* 287 antigen recognize *N. gonorrhoeae* F62 strain (FIG. 2B, compared to negative control shown in FIG. 2A) and induce complement deposition (FIG. 2D, compared to negative control shown in FIG. 2C).

The inventors have found that vaccine antigens, including those used in the meningitis B vaccine BEXSERO®, induce bactericidal antibodies against *N. gonorrhoeae* (NG) (see Examples 1-7 and 9).

Despite the marked differences in disease manifestation, based on DNA-DNA hybridisation there is 80-90% genetic homology in primary sequences between *Neisseria gonorrhoeae* and *Neisseria meningitidis*. Most virulence factors present in one have an equivalent in the other [9], providing a biologically plausible mechanism for cross-protection. However, genetic typing alone is insufficient to predict strain coverage, even between strains of *N. meningitidis* [10].

The NZ MeNZB™ vaccine was a preparation of the OMV of the epidemic strain of group B Meningococcal NZ98/254, B:4:P1.7b,4.

The BEXSERO® product (described in references 11 to 14; also known as 4CMenB) has been designed to immunize against serogroup B meningococcus. BEXSERO® contains the same OMVs as are found in the MeNZB™ vaccine (referred to herein as OMVnz). In addition, BEXSERO® comprises five meningococcal antigens: NHBA (287; subvariant 1.2), fHbp (741; subvariant 1.1), NadA (961; subvariant 3.1), GNA1030 (953) and GNA2091 (936). Four of these antigens are present as fusion proteins (an NHBA-GNA1030 fusion protein (287-953) and a GNA2091-fHbp (936-741) fusion protein). BEXSERO® includes 50 μg of each of NHBA, NadA and fHbp, adsorbed onto 1.5 mg aluminium hydroxide adjuvant, and with 25 μg OMVs from *N. meningitidis* strain NZ98/254.

The inventors have now shown that the BEXSERO® product induces an immune response that is cross-reactive for *N. gonorrhoeae*. BEXSERO® has been shown to elicit bactericidal antibodies against *N. gonorrhoeae* (Example 3), and to induce cellular immune responses with Th1 profiles associated with faster gonococcus clearance and resistance to gonococcal infection in an animal model (Example 9). It has also been shown that BEXSERO® is able to impair adhesion of gonococci to human cervical epithelial cells (Example 4).

In addition, the inventors have also shown that individual protein antigen components of BEXSERO® are capable of inducing an effective immune response against *N. gonorrhoeae*. In particular, the meningococcal NHBA antigen (287) has been shown to induce bactericidal antibodies against *N. gonorrhoeae* (Examples 1, 2 and 5). Furthermore, the inventors have found that the meningococcal accessory proteins GNA1030 (953) and GNA2091 (936), which are present as fusions with NHBA and fHbp respectively in BEXSERO®, are also capable of eliciting bactericidal antibodies against *N. gonorrhoeae* (Example 6).

Therefore the inventors have surprisingly found that meningitis B vaccine BEXSERO® and related vaccines comprising component antigens of BEXSERO® are also expected to provide protection against infection and disease with *N. gonorrhoeae*.

The inventors have also found that meningococcal saccharide antigens, conjugated to carrier proteins, such as capsular saccharides from one or more of serogroups A, C, W135 and/or Y can be used in combination with BEXSERO®, or one of more BEXSERO® antigens, to induce a bactericidal immune response against *N. gonorrhoeae* (Example 7).

The inventors have also found that gonococcal antigens elicit functional antibodies with strong and specific bactericidal activity against *N. gonorrhoeae*. It has been shown that immunization with gonococcal-derived NHBA and/or gonococcal-derived OMVs induces the bactericidal activity against *N. gonorrhoeae* (Examples 1 and 8, respectively).

Furthermore, gonococcal-derived OMVs have been found to induce cellular immune responses with Th1 profiles associated with faster gonococcus clearance and resistance to gonococcal infection in an animal model (Example 9).

As used herein, "neisserial antigen" refers to an antigen from either *N. meningitides* or *N. gonorrhoeae*.

Thus, one aspect of the invention provides a method for immunizing a subject in need thereof against *Neisseria gonorrhoeae* by administering an immunogenic composition comprising one or more of the following:
  (i) a neisserial NHBA antigen;
  (ii) a neisserial fHbp antigen;
  (iii) a neisserial NadA antigen;
  (iv) a neisserial GNA1030 antigen;
  (v) a neisserial GNA2091 antigen;
  (vi) one or more of (i) to (v) above in combination with conjugated capsular saccharide from one or more of meningococcal serogroups A. C, W135 and/or Y.

Similarly, the invention provides an immunogenic composition for use in immunizing a subject in need thereof against *Neisseria gonorrhoeae*, wherein the immunogenic composition comprises one or more of the following:
  (i) a neisserial NHBA antigen;
  (ii) a neisserial fHbp antigen;
  (iii) a neisserial NadA antigen;
  (iv) a neisserial GNA1030 antigen;
  (v) a neisserial GNA2091 antigen;
  (vi) one or more of (i) to (v) above in combination with conjugated capsular saccharide from one or more of meningococcal serogroups A, C, WI 35 and/or Y.

Also, the invention provides the use of one or more of the following in the manufacture a medicament for immunizing a subject against *Neisseria gonorrhoeae*:

(i) a neisserial NHBA antigen;
(ii) a neisserial fHbp antigen;
(iii) a neisserial NadA antigen;
(iv) a neisserial GNA1030 antigen;
(v) a neisserial GNA2091 antigen;
(vi) one or more of (i) to (v) above in combination with conjugated capsular saccharide from one or more of meningococcal serogroups A, C, W135 and/or Y.

In some embodiments the immunogenic composition may include neisserial outer membrane vesicles; in other embodiments the immunogenic composition is free from neisserial outer membrane vesicles. Where the immunogenic composition includes neisserial outer membrane vesicles in combination with one or more of antigens (i) to (v) above, then the composition preferably includes one or more of the antigen(s) (i) to (v) separate from the OMV component e.g. in soluble form.

Components (i) to (v) are preferably meningococcal antigens. However, in some cases, one or more of these antigens may be gonococcal antigens. In a particularly preferred embodiment, the immunogenic composition comprises a gonococcal NHBA antigen.

Other preferred immunogenic compositions for use in the invention comprise a meningococcal NHBA antigen, a meningococcal fHbp antigen and a meningococcal NadA antigen. Such compositions preferably also comprise meningococcal OMVs. A particularly preferred composition for use according to the invention is the BEXSERO® vaccine composition.

Other preferred immunogenic compositions for use in the invention comprise a meningococcal NHBA antigen, and one or more accessory protein antigens selected from a GNA1030 antigen and a GNA2091 antigen. Such compositions preferably also comprise meningococcal OMVs.

Other preferred immunogenic compositions for use in the invention comprise a meningococcal NHBA antigen, a meningococcal fHbp antigen and a meningococcal NadA antigen in combination with conjugated capsular saccharides from meningococcal serogroups A, C, W135 and Y. Such compositions preferably also comprise meningococcal OMVs.

A particularly preferred immunogenic composition for immunizing a subject against *Neisseria gonorrhoeae* according to the invention comprises BEXSERO® and MENVEO®1). Such immunogenic compositions comprise antigens against each of the meningococcal A, B, C, W135 and Y serotypes.

Another aspect of the invention provides a method for immunizing a subject in need thereof against *Neisseria gonorrhoeae* by administering an immunogenic composition comprising gonococcal outer membrane vesicles (OMVs).

Similarly, the invention provides an immunogenic composition for use in immunizing a subject in need thereof against *Neisseria gonorrhoeae*, wherein the immunogenic composition comprises gonococcal outer membrane vesicles (OMVs).

Also, the invention provides for the use of gonococcal outer membrane vesicles (OMVs) in the manufacture a medicament for immunizing a subject against *Neisseria gonorrhoeae*.

In these aspects of the invention, the immunogenic composition or medicament comprising gonococcal OMVs may also comprise one or more of (i) a neisserial NHBA antigen (ii) a neisserial fHbp antigen; (iii) a neisserial NadA antigen; (iv) a neisserial GNA1030 antigen; (v) a neisserial GNA2091 antigen; (vi) a conjugated capsular saccharide from one or more of meningococcal serogroups A. C, W135; and (vii) meningococcal OMVs.

In a preferred embodiment of the invention, the immunogenic composition or medicament comprises gonococcal OMVs and gonococcal NHBA.

Where the immunogenic composition or medicament includes neisserial OMVs in combination with one or more protein antigens, said one or more of the protein antigen(s) are preferably separate from the OMV component e.g. in soluble form.

Protection Against *N. gonorrhoeae*

The invention is used to immunize subjects against infection and/or disease caused by *Neisseria gonorrhoeae* (e.g. gonorrhoea and related complications such as pelvic inflammatory disease, as well as asymptomatic infection with *N. gonorrhoeae*), such that recipients of the immunogenic composition mount an immune response which provides protection against infection by and/or disease due to *Neisseria gonorrhoeae* bacteria.

Therefore, immunogenic compositions according to the invention are used in prophylactic methods for immunizing subjects against infection and/or disease caused by *Neisseria gonorrhoeae*. The immunogenic compositions may also be used in therapeutic methods (i.e. to treat *Neisseria gonorrhoeae* infection).

Protection against *N. gonorrhoeae* can be measured epidemiologically e.g. in a clinical trial, but it is convenient to use an indirect measure to confirm that an immunogenic composition elicits a serum bactericidal antibody (SBA) response in recipients. In the SBA assay, sera from recipients of the composition are incubated with target bacteria (in the present invention, *N. gonorrhoeae*) in the presence of complement (preferably human complement, although baby rabbit complement is often used instead) and killing of the bacteria is assessed at various dilutions of the sera to determine SBA activity. Results observed in the SBA assay can be reinforced by carrying out a competitive SBA assay to provide further indirect evidence of the immunogenic activity of antigen(s) of interest. In the competitive SBA assay, sera from recipients of the immunogenic composition containing the antigen(s) are pre-incubated with said antigen(s), and subsequently incubated with target bacteria in the presence of human complement. Killing of the bacteria is then assessed, and will be reduced or abolished if bactericidal antibodies in the recipients' sera bind to the antigens of interested during the pre-incubation phase and are therefore not available to bind to surface antigen on the bacteria.

It is not necessary that the composition should protect against each and every strain of *N. gonorrhoeae*, or that each and every recipient of the composition must be protected. Such universal protection is not the normal standard in this field. Rather, protection is normally assessed against a panel of reference laboratory strains e.g. FA1090, MS11 and F62, often selected on a country-by-country basis and perhaps varying with time, and is measured across a population of recipients. Set against the backdrop that there is no vaccine currently available to protect against gonorrhoea, even a low level of cross-protection could make vaccination worthwhile. Indeed, modelling of the theoretical impact of a meningococcal vaccine on rates of *N. gonorrhoeae* infection suggest that such vaccination would be cost-effective even at a vaccine efficacy against *N. gonorrhoeae* as low as 20% (or even 10% if antibiotic resistance were to rise substantially) [15].

As well as being immunized against *N. gonorrhoeae*, recipients may also be immunized against one or more serogroups of *N. meningitidis* e.g. one or more of serogroups A. B, C, W135. X and/or Y (even in the absence of capsular saccharides from serogroups A. C, W135 &/or Y). For instance, reference 16 reports that the antigens in BEX-SERO® can protect against serogroup Y, reference 17 suggests that fHbp might provide protection beyond serogroup B alone, and reference 18 teaches that the antigens in BEXSERO® can protect against serogroup X.

The Immunogenic Composition

The invention uses an immunogenic composition (e.g. a vaccine) to protect subjects against *N. gonorrhoeae*. The composition includes an immunogenic amount of at least one of the antigens or combinations of antigens provided above.

The composition does not include an immunogenic amount of *N. gonorrhoeae* capsular saccharide i.e. protection against *N. gonorrhoeae* cannot be explained by an anti-saccharide response. *N. gonorrhoeae* capsular saccharide is absent as free saccharide, conjugated saccharide, or membrane-located saccharide (e.g. in OMVs). Preferably, the composition is also free of unconjugated capsular saccharide from *N. meningitidis* serogroup A and/or C. The composition is non-pathogenic and does not comprise whole cells of *N. meningitidis* or *N. gonorrhoeae*.

A preferred composition includes each of: (i) a NHBA antigen comprising or consisting of amino acid sequence SEQ ID NO: 8 e.g. SEQ ID NO: 9; (ii) a fHbp antigen comprising or consisting of amino acid sequence SEQ ID NO: 6 e.g. SEQ ID NO: 7, and (iii) a NadA antigen comprising amino or consisting of acid sequence SEQ ID NO: 10. BEXSERO® is one such composition. Such a composition preferably further comprises meningococcal OMVs.

Although SEQ ID NOs: 6 (meningococcal fHbp), 8 (meningococcal NHBA) and 10 (meningococcal NadA) are useful amino acid sequences in a combination, the invention is not limited to these precise sequences. Thus 1, 2, or all 3 of these amino acid sequences can independently be modified by up to 5 single amino changes (i.e. 1, 2, 3, 4 or 5 single amino acid substitutions, deletions and/or insertions) provided that the modified sequence can elicit antibodies which still bind to a polypeptide consisting of the unmodified sequence.

The polypeptides (or a subset thereof, e.g. non-OMV or soluble polypeptides) in a composition may be present at substantially equal masses i.e. the mass of each of them is within +5% of the mean mass of all the polypeptides in the composition (or the mean mass of the selected subset of polypeptides). For example, where the composition includes NHBA, fHbp and NadA, they may be may be present at substantially equal masses, e.g. at a mass ratio of a:b:c, where each of a, b & c is between 0.95 and 1.05.

NadA is absent in all *N. gonorrhoeae* thus far studied (see references 19 and 20).

The fHbp gene in gonococcal strains studied thus far differs from the equivalent meningococcal gene in part by the insertion of a G residue at position 40, which results in a frame-shift causing the loss of the lipobox motif (see references 10 and 20). In addition, the gonococcal fHbp of at least one strain of *N. gonorrhoeae* is not surface expressed and does not bind to factor H [21]. Accordingly, it is expected that these two antigens are likely to give only narrow protection (if any) against a more limited range of gonococcal strains, compared to the protection offered by immunization with e.g. NHBA, which is expressed on the surface of gonococcus (see Example 4). For this reason, an immunogenic composition based on NadA alone, fHbp alone, or a combination of NadA and fHbp only is not preferred for use with the present invention. If either or both of these antigens are used, preferably one or more of the following components is additionally included in the immunogenic composition: NHBA neisserial antigen; GNA1030 neisserial antigen; GNA2091 neisserial antigen; conjugated capsular saccharide from one or more of meningococcal serogroups A. C, W135 and/or Y.

NHBA (Neisserial Heparin Binding Antigen)

NHBA was included in the published genome sequence for meningococcal serogroup B strain MC58 [22] as gene NMB2132 (GenBank accession number GI:7227388; SEQ ID NO: 4 herein). Sequences of NHBA from many strains have been published since then. For example, allelic forms of NHBA (referred to as protein '287') can be seen in FIGS. 5 and 15 of reference 23, and in example 13 and FIG. 21 of reference 24 (SEQ IDs 3179 to 3184 therein). Various immunogenic fragments of NHBA have also been reported. The protein was confirmed as a heparin binding protein, and named NHBA, in reference 25.

References to NHBA herein include truncated variants of NHBA, wherein the N-terminus of the wild-type NHBA polypeptide sequence has been deleted up to and including its poly-glycine sequence (i.e. deletion of residues 1 to 24 in meningococcal strain MC58 (SEQ ID No. 4)). The resulting truncated variant is sometimes distinguished herein by the use of a 'ΔG' prefix. This deletion can enhance expression. The 'ΔG' variant of meningococcal NHBA is referred to herein as SEQ ID NO. 8. The 'ΔG' variant of gonococcal NHBA is referred to herein as SEQ ID NO. 15.

Preferred NHBA antigens for use with the invention comprise an amino acid sequence: (a) having 70% or more identity (e.g. 70%, 75%, 80%, 85%, 90%, 91%, 92%, 93%, 94%, 95%, 96%, 97%, 98%, 99%, 99.5% or more) to SEQ ID NO: 4; and/or (b) comprising a fragment of at least 'n' consecutive amino acids of SEQ ID NO: 4, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 4. Particularly preferred NHBA antigens for use with the invention comprise the amino acid sequence of SEQ ID NO:8.

The most useful meningococcal NHBA antigens will, when administered to a subject, elicit antibodies that bind to a meningococcal polypeptide consisting of amino acid sequence SEQ ID NO: 4. Advantageous meningococcal NHBA antigens for use with the invention can elicit bactericidal anti-gonococcal antibodies after administration to a subject.

Other preferred NHBA antigens for use with the invention comprise a gonococcal NHBA sequence, e.g. an amino acid sequence: (a) having 70% or more identity (e.g. 70%, 75%, 80%, 85%, 90%, 91%, 92%, 93%, 94%, 95%, 96%, 97%, 98%, 99%, 99.5% or more) to SEQ ID NO: 15; and/or (b) comprising a fragment of at least 'n' consecutive amino acids of SEQ ID NO: 15, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 15.

A polypeptide including a neisserial NHBA antigen sequence (whether meningococcal or gonococcal) can include that sequence alone, or it can be a fusion protein. One useful fusion partner for a NHBA sequence is the GNA1030 (953) polypeptide, which will normally be downstream of the NHBA sequence. Thus the NHBA antigen can be present in a composition of the invention as a NHBA-GNA1030 fusion (e.g. SEQ ID NO: 9 for a meningococcal NHBA antigen).

NadA (Neisserial Adhesin A)

The NadA antigen was included in the published genome sequence for meningococcal serogroup B strain MC58 [22] as gene NMB1994 (GenBank accession number GI:7227256; SEQ ID NO: 5 herein). The sequences of NadA antigen from many strains have been published since then, and the protein's activity as a Neisserial adhesin has been well documented. Various immunogenic fragments of NadA have also been reported. The protein was confirmed as an adhesin, and named NadA, in reference 26.

Preferred NadA antigens for use with the invention comprise an amino acid sequence: (a) having 70% or more identity (e.g. 70%, 75%, 80%, 85%, 90%, 91%, 92%, 93%, 94%, 95%, 96%, 97%, 98%, 990%, 99.5% or more) to SEQ ID NO: 5; and/or (b) comprising a fragment of at least 'n' consecutive amino acids of SEQ ID NO: 5, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 5.

The most useful NadA antigens can elicit antibodies which, after administration to a subject, can bind to a meningococcal polypeptide consisting of amino acid sequence SEQ ID NO: 5. SEQ ID NO: 10 is one such fragment. Particularly preferred NadA antigens for use according to the invention comprise SEQ ID NO:10.

fHbp (Factor H Binding Protein)

The fHbp antigen has been characterized in detail. It has also been known as protein '741' (SEQ IDs 2535 & 2536 in ref. 24), 'NMB1870', 'GNA1870' [27-29] 'P2086', 'LP2086' or 'ORF2086' [30-32]. It is expressed across many meningococcal serogroups, in which it is a lipoprotein. The structure of fHbp's C-terminal immunodominant domain ('fHpC') has been determined by NMR [33]. This part of the protein forms an eight-stranded β-barrel, whose strands are connected by loops of variable lengths. The barrel is preceded by a short α-helix and by a flexible N-terminal tail. The protein was confirmed as a factor H binding protein, and named fHbp, in reference 34. The fHbp antigen is also present in *N. gonorrhoeae*, and the major differences between meningococcal and gonococcal fHbp are at the N-terminus [10]. In *N. gonorrhoeae*, the homologue of meningococcal fHbp is also known as Ghfp.

The fHbp antigen falls into three distinct variants [35] and it has been found that for meningococci, serum raised against a given family is bactericidal within the same family, but is not active against strains which express one of the other two families i.e. there is intra-family cross-protection, but not inter-family cross-protection. The invention can use a single fHbp variant, but to provide broader coverage a composition can usefully include a fHbp from two or three of the variants. Known *N. gonorrhoeae* fHbp sequences are from variant 3 [10].

Where a composition comprises a single fHbp antigen it may include one of the following:
  (a) a first polypeptide comprising a first amino acid sequence, where the first amino acid sequence comprises an amino acid sequence (i) having at least a % sequence identity to SEQ ID NO: 1 and/or (ii) consisting of a fragment of at least x contiguous amino acids from SEQ ID NO: 1;
  (b) a second polypeptide, comprising a second amino acid sequence, where the second amino acid sequence comprises an amino acid sequence (i) having at least b % sequence identity to SEQ ID NO: 2 and/or (ii) consisting of a fragment of at least y contiguous amino acids from SEQ ID NO: 2;
  (c) a third polypeptide, comprising a third amino acid sequence, where the third amino acid sequence comprises an amino acid sequence (i) having at least c % sequence identity to SEQ ID NO: 3 and/or (ii) consisting of a fragment of at least z contiguous amino acids from SEQ ID NO: 3.

Where a composition comprises two different meningococcal fHbp antigens, it may include a combination of: (i) a first and second polypeptide as defined above; (ii) a first and third polypeptide as defined above; or (iii) a second and third polypeptide as defined above. A combination of a first and third polypeptide is preferred. If a single fHbp antigen is used, it is preferred that it is a first or a third polypeptide as described above.

In other embodiments a composition comprises three different meningococcal fHbp antigens, with first, second and third polypeptides as defined above.

Where a composition comprises two or three different meningococcal fHbp antigens, although these may share some sequences in common, the first, second and third polypeptides have different fHbp amino acid sequences.

A polypeptide comprising the first amino acid sequence will, when administered to a subject, elicit an antibody response comprising antibodies that bind to the wild-type meningococcus protein having mature amino acid sequence SEQ ID NO: 1 (strain MC58). In some embodiments some or all of these antibodies do not bind to the wild-type meningococcus protein having mature amino acid sequence SEQ ID NO: 2 or to the wild-type meningococcus protein having mature amino acid sequence SEQ ID NO: 3.

A polypeptide comprising the second amino acid sequence will, when administered to a subject, elicit an antibody response comprising antibodies that bind to the wild-type meningococcus protein having mature amino acid sequence SEQ ID NO: 2 (strain 961-5945). In some embodiments some or all of these antibodies do not bind to the wild-type meningococcus protein having mature amino acid sequence SEQ ID NO: 1 or to the wild-type meningococcus protein having mature amino acid sequence SEQ ID NO: 3.

A polypeptide comprising the third amino acid sequence will, when administered to a subject, elicit an antibody response comprising antibodies that bind to the wild-type meningococcus protein having mature amino acid sequence SEQ ID NO: 3 (M1239). In some embodiments some or all of these antibodies do not bind to the wild-type meningococcus protein having mature amino acid sequence SEQ ID NO: 1 or to the wild-type meningococcus protein having mature amino acid sequence SEQ ID NO: 2.

In some embodiments the fragment of at least x contiguous amino acids from SEQ ID NO: 1 is not also present within SEQ ID NO: 2 or within SEQ ID NO: 3. Similarly, the fragment of at least y contiguous amino acids from SEQ ID NO: 2 might not also be present within SEQ ID NO: 1 or within SEQ ID NO: 3. Similarly, the fragment of at least z contiguous amino acids from SEQ ID NO: 3 might not also be present within SEQ ID NO: 1 or within SEQ ID NO: 2. In some embodiments, when said fragment from one of SEQ ID NOs: 1 to 3 is aligned as a contiguous sequence against the other two SEQ ID NOs, the identity between the fragment and each of the other two SEQ ID NOs is less than 75% e.g. less than 70%, less than 65%, less than 60%, etc.

The value of a is at least 80 e.g. 82, 84, 86, 88, 90, 92, 94, 95, 96, 97, 98, 99 or more. The value of b is at least 80 e.g. 82, 84, 86, 88, 90, 92, 94, 95, 96, 97, 98, 99 or more. The value of c is at least 80 e.g. 82, 84, 86, 88, 90, 92, 94, 95, 96, 97, 98, 99 or more. The values of a, b and c may be the same or different. In some embodiments, a b and c are identical.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z may be the same or different. In some embodiments, x y and z are identical.

Fragments preferably comprise an epitope from the respective SEQ ID NO: sequence. Other useful fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of the respective SEQ ID NO: while retaining at least one epitope thereof.

Amino acid sequences used with the invention may, compared to SEQ ID NOs: 1, 2 or 3, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may have one or more (e.g. 1, 2, 3, 4, 5, 6, 7, 8, 9, 10, etc.) single amino acid deletions relative to a reference sequence. The polypeptides may also include one or more (e.g. 1, 2, 3, 4, 5, 6, 7, 8, 9, 10, etc.) insertions (e.g. each of 1, 2, 3, 4 or 5 amino acids) relative to a reference sequence.

A useful first amino acid sequence has at least 85% identity (e.g. ≥90%, 95% or 100%) to SEQ ID NO: 1. Another useful first amino acid sequence has at least 95% identity (e.g. ≥98% or 100%) to SEQ ID NO: 12. Preferred fHbp sequences for use according to the invention comprise SEQ ID NO:6.

A useful third amino acid sequence has at least 85% identity (e.g. ≥90%, 95% or 100%) to SEQ ID NO: 3. Another useful third amino acid sequence has at least 95% identity (e.g. ≥98% or 100%) to SEQ ID NO: 11.

Combinations comprising a mixture of first and third sequences based around SEQ ID NOs: 11 and 12 (or their close variants) are particularly useful. Thus a composition may comprise a polypeptide comprising amino acid sequence SEQ ID NO: 11 and a further polypeptide comprising amino acid sequence SEQ ID NO: 12.

Another useful fHbp which can be used with the invention is one of the modified forms disclosed, for example, in reference 36 e.g. comprising SEQ ID NO: 20 or 23 therefrom. These modified forms can use a single fHbp polypeptide to elicit antibody responses which are broadly bactericidal against various fHbp variants. SEQ ID NO: 77 in reference 36 is another useful fHbp sequence which can be used.

fHbp antigens used with the invention can be lipidated e.g. at a N-terminus cysteine residue. In other embodiments they will not be lipidated, and may include amino acid sequences upstream of the natural mature N-terminal cysteine. SEQ ID NOs: 1-3 and 11-12 begin with the cysteine from the natural N-terminus of the relevant mature fHbp polypeptides. For lipidated fHBPs, lipids attached to cysteines will usually include palmitoyl residues e.g. as tripalmitoyl-S-glyceryl-cysteine (Pam3Cys), dipalmitoyl-S-glyceryl cysteine (Pam2Cys), N-acetyl (dipalmitoyl-S-glyceryl cysteine), etc.

Administration of a fHBP will preferably elicit antibodies which can bind to a meningococcal polypeptide consisting of amino acid sequence SEQ ID NO: 1, 2 or 3. Advantageous fHBP antigens for use with the invention can elicit bactericidal anti-gonococcal antibodies after administration to a subject.

The total amount of a fHbp polypeptide will usually be between 1 and 500 μg/dose e.g. between 60 and 200 μg/dose or between 120 and 500 μg/ml.

A polypeptide including the fHbp antigen sequence can include that sequence alone, or it can be a fusion polypeptide. One useful fusion partner for a fHbp sequence is the GNA2091 polypeptide, which will normally be upstream of the fHbp sequence. Thus the fHbp antigen can be present in a composition of the invention as a GNA2091-fHbp fusion e.g. SEQ ID NO: 7.

Compositions used with the invention may also include an fHIbp fusion protein comprising 2 or 3 of the first, second and third amino acid sequences defined at (a) to (c) above.

Compositions used with the invention may also include an fHbp protein that is mutated relative to SEQ ID NO:1, 2 or 3 (fHbp variant 1, 2 or 3 respectively) to decrease binding to human factor H (fH). Suitable mutations are disclosed in reference 37.

GNA1030 Antigens

'GNA1030' protein from meningococcus serogroup B is disclosed as '953' in reference 24 (SEQ IDs 2917 & 2918 therein) and as 'NMB1030' in reference 22 (see also GenBank accession number GI:7226269). The corresponding protein in serogroup A [38] has GenBank accession number 7380108.

When used according to the present invention, GNA1030 protein may take various forms.

Preferred forms of GNA1030 are truncation or deletion variants, such as those disclosed in references 39, 40 and 41. In particular, the N-terminus leader peptide of GNA1030 may be deleted (i.e. deletion of residues 1 to 19 for strain MC58 [SEQ ID NO:13]) to give GNA1030$^{(NL)}$.

Preferred GNA1030 sequences have 50% or more identity (e.g. 60%, 70%, 80%, 90%, 95%, 99% or more) to SEQ ID NO:13. This includes GNA1030 variants (e.g. allelic variants, homologs, orthologs, paralogs, mutants, etc.). Allelic forms of GNA1030 can be seen in FIG. 19 of reference 23.

Other preferred GNA1030 sequences comprise at least n consecutive amino acids from SEQ ID NO:13, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from GNA1030, in which case detection of the epitope in a pathogen of interest may be performed using a monoclonal antibody to the epitope. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:13.

GNA2091 Antigens

'GNA2091' protein from meningococcus serogroup B is disclosed as protein 936 in reference 24 (SEQ IDs 2883 &

2884) and as 'NMB2091' in reference 22 (see also GenBank accession number GI:7227353). The corresponding gene in serogroup A [38] has GenBank accession number 7379093.

When used according to the present invention, GNA2091 protein may take various forms. Preferred forms of GNA2091 are truncation or deletion variants, such as those disclosed in references 39, 40 and 41. In particular, the N-terminus leader peptide of GNA2091 may be deleted (i.e. deletion of residues 1 to 23 for strain MC58 [SEQ ID NO:14]) to give GNA2091NL.

Preferred GNA2091 sequences have 50% or more identity (e.g. 60%, 70%, 80%, 90%, 95%, 99% or more) to SEQ ID NO:14. This includes variants (e.g. allelic variants, homologs, orthologs, paralogs, mutants etc).

Other preferred GNA2091 sequences comprise at least n consecutive amino acids from SEQ ID NO:14, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope from GNA2091, in which case detection of the epitope in a pathogen of interest may be performed using a monoclonal antibody to the epitope. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:14.

Outer Membrane Vesicles

In some aspects and embodiments the immunogenic composition of the invention includes neisserial (meningococcal or gonococcal) OMVs. Optionally, in such OMV-containing embodiments, the composition includes at least one of the above-listed antigens (i.e. NHBA, NadA, GNA1030 or GNA2091) separate from the OMV component e.g. in soluble form. Thus these compositions are prepared by mixing OMVs with one or more soluble antigen(s), which contrasts with the approach taken in references 42 and 43.

Where a composition includes OMVs, these OMVs can be any proteoliposomic vesicle obtained by disruption of or blebbing from a meningococcal or gonococcal outer membrane to form vesicles therefrom that retain antigens from the outer membrane. Thus this term includes, for instance, OMVs (sometimes referred to as 'blebs'), microvesicles (MVs), 'native OMVs' ('NOMVs') extracted from cells using detergent-free methods, and detergent-extracted OMVs (dOMVs), such as OMVs extracted from cells using deoxycholate treatment. Various such vesicles are known in the art (e.g. see references 44 to 58) and any of these can be included within a composition of the invention.

The mass of OMVs is measured as the amount of total protein.

Preferred meningococcal OMVs comprise a PorA serotype 1.4. Preferably, the OMVs comprise a PorA variable region epitope 1.7-2 (VR1) and/or 1.4 (VR2). OMVs comprising both of these epitopes are more preferred (i.e. P1.7-2,4). OMVs obtained from strain NZ98/254 are particularly preferred.

Meningococcal Saccharide Antigens

A composition can include one or more meningococcal saccharide antigens, conjugated to carrier proteins. Thus, for instance, a composition might include one or more capsular saccharides from serogroups A, C, W135 and/or Y. For instance, the composition might include the conjugates which are present in the MENVEO®, MENACTRA®, or NIMENRIX® products (all of which include conjugated capsular saccharides for each of serogroups A, C, W135 and Y).

Multivalent compositions comprising conjugated saccharide antigens from 2, 3, or 4 of serogroups A, C, W135 and Y are preferred e.g. A+C, C+Y, W135+Y, A+W135+Y, A+C+W135+Y, etc. Compositions including a conjugated saccharide antigen from at least serogroup C are preferred (e.g. A+C), as are compositions including at least a conjugated saccharide antigen from serogroup Y. Compositions including conjugated saccharides from all four of serogroups A. C, W135 and Y are most preferred.

Where compositions include a meningococcal capsular saccharide from meningococcal serogroup A, C, W135 and/or Y (that is not part of an OMV component of the immunogenic composition), the capsular saccharide is conjugated to a carrier protein.

The capsular saccharide of serogroup A meningococcus is a homopolymer of (α1→6)-linked N-acetyl-D-mannosamine-1-phosphate, with partial O-acetylation in the C3 and C4 positions. Acetylation at the C-3 position can be 70-95%. Conditions used to purify the saccharide can result in de-O-acetylation (e.g. under basic conditions), but it is useful to retain OAc at this C-3 position. In some embodiments, at least 50% (e.g. at least 60%, 70%, 80%, 90%, 95% or more) of the mannosamine residues in a serogroup A saccharides are O-acetylated at the C-3 position. Acetyl groups can be replaced with blocking groups to prevent hydrolysis [59], and such modified saccharides are still serogroup A saccharides within the meaning of the invention.

The serogroup C capsular saccharide is a homopolymer of (α2→9)-linked sialic acid (N-acetyl neuraminic acid, or 'NeuNAc'). The saccharide structure is written as →9)-Neu p NAc 7/8 OAc-(α2→. Most serogroup C strains have O-acetyl groups at C-7 and/or C-8 of the sialic acid residues, but about 15% of clinical isolates lack these O-acetyl groups [60.61]. The presence or absence of OAc groups generates unique epitopes, and the specificity of antibody binding to the saccharide may affect its bactericidal activity against O-acetylated (OAc+) and de-O-acetylated (OAc−) strains [62-64]. Serogroup C saccharides used with the invention may be prepared from either OAc+ or OAc− strains. Licensed Men-C conjugate vaccines include both OAc− (NEISVAC-C™) and OAc+(MENJUGATE™ & MENINGITEC™) saccharides. In some embodiments, strains for production of serogroup C conjugates are OAc+ strains, e.g. of serotype 16, serosubtype P1.7a,1, etc. Thus C:16:P1.7a,1 OAc+ strains may be used. OAc+ strains in serosubtype P1.1 are also useful, such as the C11 strain.

The serogroup W135 saccharide is a polymer of sialic acid-galactose disaccharide units. Like the serogroup C saccharide, it has variable O-acetylation, but at sialic acid 7 and 9 positions [65]. The structure is written as: →4)-D-Neup5Ac(7/9OAc)-α-(2→6)-D-Gal-α-(1→.

The serogroup Y saccharide is similar to the serogroup W135 saccharide, except that the disaccharide repeating unit includes glucose instead of galactose. Like serogroup W135, it has variable O-acetylation at sialic acid 7 and 9 positions [65]. The serogroup Y structure is written as: →4)-D-Neup5Ac(7/9OAc)-α-(2→6)-D-Glc-α-(1→.

The saccharides used according to the invention may be O-acetylated as described above (e.g. with the same O-acetylation pattern as seen in native capsular saccharides), or they may be partially or totally de-O-acetylated at one or more positions of the saccharide rings, or they may be hyper-O-acetylated relative to the native capsular saccharides.

The saccharide moieties in conjugates may comprise full-length saccharides as prepared from meningococci, and/or may comprise fragments of full-length saccharides i.e. the saccharides may be shorter than the native capsular saccharides seen in bacteria. The saccharides may thus be depolymerized, with depolymerisation occurring during or after saccharide purification but before conjugation. Depolymensation reduces the chain length of the saccharides. One depolymerisation method involves the use of hydrogen peroxide [66]. Hydrogen peroxide is added to a saccharide (e.g. to give a final $H_2O_2$ concentration of 1%), and the mixture is then incubated (e.g. at about 55° C.) until a desired chain length reduction has been achieved. Another depolymerisation method involves acid hydrolysis [66]. Other depolymerisation methods are known in the art. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides. In some embodiments, saccharides have the following range of average degrees of polymerisation (Dp): A=10-20; C=12-22; W135=15-25; Y=15-25. In terms of molecular weight, rather than Dp, useful ranges are, for all serogroups: <100 kDa; 5 kDa-75 kDa; 7 kDa-50 kDa; 8 kDa-35 kDa; 12 kDa-25 kDa; 15 kDa-22 kDa (saccharide MW).

In some embodiments, the average molecular weight for saccharides from each of meningococcal serogroups A, C, W135 and Y may be more than 50 kDa e.g. ≥75 kDa, ≥100 kDa, ≥110 kDa, ≥20 kDa, ≥130 kDa, etc. [67], and even up to 1500 kDa, in particular as determined by MALLS. For instance: a Men-A saccharide may be in the range 50-500 kDa e.g. 60-80 kDa; a Men-C saccharide may be in the range 100-210 kDa; a Men-W135 saccharide may be in the range 60-190 kDa e.g. 120-140 kDa; and/or a Men-Y saccharide may be in the range 60-190 kDa e.g. 150-160 kDa.

The mass of meningococcal saccharide per serogroup in the immunogenic composition will usually be between 1 µg and 20 µg e.g. between 2 and 10 µg per serogroup, or about 4 µg or about 5 µg or about 10 µg. Where conjugates from more than one serogroup are included then they may be present at substantially equal masses e.g. the mass of each serogroup's saccharide is within +10% of each other. As an alternative to an equal ratio, a double mass of serogroup A saccharide may be used. Thus a vaccine may include Men-A saccharide at 10 µg and Men-C, -W135 and -Y saccharides at 5 µg each.

Typical carrier proteins for use in conjugates are bacterial toxins, such as diphtheria toxin [e.g. see chapter 13 of ref. 68; refs. 69-72] (or its CRM197 mutant [73-76]) and tetanus toxin, usually in toxoid form (e.g. obtained by treatment with an inactivating chemical, such as formalin or formaldehyde). Other suitable carrier proteins include the *N. meningitidis* outer membrane protein complex [77], synthetic peptides [78,79], heat shock proteins [80.81], pertussis proteins [82,83], cytokines [84], lymphokines [84], hormones [84], growth factors [84], artificial proteins comprising multiple human CD4+ T-cell epitopes from various pathogen-derived antigens [85] such as N19 [86], protein D from *H. influenzae* [87-89], pneumolysin [90] or its non-toxic derivatives [91], pneumococcal surface protein PspA [92], iron-uptake proteins [93], toxin A or B from *C. difficile* [94], recombinant *Pseudomonas aeruginosa* exoprotein A (rEPA) [95], etc.

A single carrier protein molecule may carry saccharides from multiple different serogroups [96], but this arrangement is not preferred. Serotype conjugates are preferably prepared separately and then mixed. Thus it is preferred not to use a single protein carrying multiple serogroups (cf. references 96 & 97). After mixing, the concentration of the mixed conjugates can be adjusted e.g. with sterile pyrogen-free, phosphate-buffered saline. Where the lyophilized component includes conjugates from more than one meningococcal serogroup then the various conjugates may use different carrier proteins (e.g. one serogroup on CRM197, another on tetanus toxoid) or they may use the same carrier protein (e.g. saccharides from two serogroups separately conjugated to CRM197 and then combined).

Four particularly preferred carrier proteins are diphtheria toxoid (Dt), tetanus toxoid (Tt), CRM197 and protein D from *H. influenzae*. These proteins are preferred because they are the main carriers currently in use in pediatric vaccines e.g. the Hib conjugates from GSK use Tt as the carrier, the HibTITER™ product uses CRM197, the pneumococcal conjugates in PREVNAR™ use CRM197, the MENACTRA™ product uses Dt, the MENJUGATE™ and MENINGITEC™ products use CRM197, and NEISVAC-C™ uses Tt.

Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5. As described in reference 98, different meningococcal serogroup conjugates in a mixture can have different saccharide:protein ratios e.g. one may have a ratio of between 1:2 & 1:5, whereas another has a ratio between 5:1 & 1:1.99. Conjugates with saccharide: protein ratio of about 1:12 or about 1:3 are useful where the carrier is Dt. In some embodiments, a conjugate ideally has a weight excess of carrier protein.

The carrier molecule may be covalently conjugated to the meningococcal saccharide directly or via a linker. Various linkers are known e.g. an adipic acid linker, which may be formed by coupling a free —$NH_2$ group (e.g. introduced to a saccharide by amination) with adipic acid (using, for example, diimide activation), and then coupling a protein to the resulting saccharide-adipic acid intermediate [99,100]. Another preferred type of linkage is a carbonyl linker, which may be formed by reaction of a free hydroxyl group of a modified glucan with CDI [101,102] followed by reaction with a protein to form a carbamate linkage. Other linkers include β-propionamido [103], nitrophenyl-ethylamine [104], haloacyl halides [105], glycosidic linkages [106], 6-aminocaproic acid [107], N-succinimidyl-3-(2-pyridyldithio)-propionate (SPDP) [108], adipic acid dihydrazide ADH [109], $C_4$ to $C_{12}$ moieties [110], etc. Carbodiimide condensation can also be used [111].

Direct linkages to the protein may comprise oxidation of the polysaccharide followed by reductive amination with the protein, as described in, for example, references 112 and 113.

As described in reference 114, a mixture can include one conjugate with direct saccharide/protein linkage and another conjugate with linkage via a linker. This arrangement applies particularly when using saccharide conjugates from different meningococcal serogroups e.g. Men-A and Men-C saccharides may be conjugated via a linker, whereas Men-W135 and Men-Y saccharides may be conjugated directly to a carrier protein.

The saccharide will typically be activated or functionalized prior to conjugation. Activation may involve, for example, cyanylating reagents [115, 116, etc.]). Other suitable techniques use active esters, carbodiimides, hydrazides, norborane, p-nitrobenzoic acid, N-hydroxysuccinimide. S—NHS, EDC, TSTU; see also the introduction to reference 117).

A useful conjugation process involves: introduction of amino groups into the saccharide (e.g. by replacing terminal =O groups with —$NH_2$) followed by derivatisation with an adipic diester (e.g. adipic acid N-hydroxysuccinimide diester) and reaction with carrier protein (e.g. CRM197).

Further details of this conjugation method can be found in reference 118. Conjugates obtainable by this method are preferred conjugates for use according to the invention.

In another useful conjugation process, a saccharide is reacted with adipic acid dihydrazide. For serogroup A, carbodiimide (EDAC) may also be added at this stage. After a reaction period, sodium cyanoborohydride is added. Derivatized saccharide can then be prepared e.g. by ultrafiltration. The derivatized saccharide is then mixed with carrier protein (e.g. with a diphtheria toxoid), and carbodiimide is added. After a reaction period, the conjugate can be recovered. Further details of this conjugation method can be found in reference 118. Conjugates obtainable by this method are preferred conjugates for use according to the invention e.g. conjugates comprising a diphtheria toxoid carrier and an adipic acid linker.

In another useful conjugation process, a saccharide is derivatized with a cyanylating reagent [116], followed by coupling to a protein (direct, or after introduction of a thiol or hydrazide nucleophile group into the carrier), without the need to use a linker. Suitable cyanylating reagents include 1-cyano-4-(dimethylamino)-pyridinium tetrafluoroborate ('CDAP'), p-nitrophenylcyanate and N-cyanotriethylammonium tetrafluoroborate ('CTEA'). CDAP is preferred, particularly where *H. influenzae* protein D is the common carrier. Direct coupling is preferred.

Administration of a conjugate preferably results in an increase in serum bactericidal assay (SBA) titre for the relevant serogroup of at least 4-fold, and preferably at least 8-fold, measured with human complement [119]. If rabbit complement is used to measure SBA titres then the titre increase is preferably at least 128-fold.

In compositions of the invention, the amount of carrier (conjugated and unconjugated) from each conjugate is preferably no more than 100 µg/ml e.g. <30 µg/ml of carrier protein from each conjugate. Preferred compositions include a total concentration of carrier (either solely for the combined meningococcal conjugates, or preferably for the composition as a whole) of less than 500 µg/ml e.g. <400 µg/ml, <300 µg/ml, <200 µg/ml, <100 µg/ml, <50 µg/ml, etc.

Where a composition includes a Hib conjugate then, in some embodiments, its mass will be substantially the same as the mean mass of meningococcal saccharide per serogroup. In some embodiments, the mass of Hib saccharide will be more than (e.g. at least 1.5×) the mean mass of meningococcal saccharide per serogroup. In some embodiments, the mass of Hib saccharide will be less than (e.g. at least 1.5×) the mean mass of meningococcal saccharide per serogroup [120].

Further Meningococcal Antigens

A composition can include one or more further meningococcal protein antigens, such as HmbR, NspA, NhhA, App, Omp85, TbpA. TbpB, and/or CuZn-superoxide dismutase.

Non-Meningococcal Antigens

A composition can include one or more non-meningococcal antigens (where the non-meningococcal antigens are not *N. gonorrhoeae* capsular saccharides as discussed above). For instance, the composition can include one or more of: (a) an antigen from *Streptococcus pneumoniae*, such as a saccharide (typically conjugated), as in the PREVNAR and SYNFLORIX products. (b) an antigen from hepatitis B virus, such as the surface antigen HBsAg; (c) an antigen from *Bordetella pertussis*, such as pertussis holotoxin (PT) and filamentous haemagluttinin (FHA) from *B. pertussis*, optionally also in combination with pertactin and/or agglutinogens 2 and 3; (d) a diphtheria antigen, such as a diphtheria toxoid; (e) a tetanus antigen, such as a tetanus toxoid; (f) a saccharide antigen from *Haemophilus influenzae* B (Hib), typically conjugated: and/or (g) inactivated poliovirus antigens.

Non-Antigen Components

In addition to its antigens, an immunogenic composition of the invention typically includes a pharmaceutically acceptable carrier, and a thorough discussion of such carriers is available in reference 121.

The pH of a composition is usually between 6 and 8, and more preferably between 6.5 and 7.5 (e.g. about 7). Stable pH may be maintained by the use of a buffer e.g. a Tris buffer, a citrate buffer, phosphate buffer, or a histidine buffer. Thus a composition will generally include a buffer. A particularly preferred buffer is a histidine buffer with a pH between 6.4 and 6.7.

A composition may be sterile and/or pyrogen-free. Compositions may be isotonic with respect to humans.

A composition comprises an immunologically effective amount of its antigen(s). Further, a single dose of the composition comprises an immunologically effective amount of OMV antigens. An 'immunologically effective amount' is an amount which, when administered to a subject, is effective for eliciting an antibody response against the antigen. This amount can vary depending upon the health and physical condition of the individual to be treated, their age, the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the mass of protein per dose. A dose of 10-500 µg (e.g. 50 µg) per antigen can be useful.

Immunogenic compositions may include an immunological adjuvant in an immune-enhancing amount, i.e., an amount sufficient to to increase the composition's immunogenicity, compared to the composition without the adjuvant component. Where the composition is a vaccine, the increase in immunogenicity may be measured either by increased vaccine efficacy or by the ability to reduce the amount of an antigen (or antigens) while maintaining a similar level of vaccine efficacy. Thus, for example, compositions may include an aluminium salt adjuvant or an oil-in-water emulsion (e.g. a squalene-in-water emulsion). Suitable aluminium salts include hydroxides (e.g. oxyhydroxides), phosphates (e.g. hydroxyphosphates, orthophosphates), (e.g. see chapters 8 & 9 of ref 122), or mixtures thereof. The salts can take any suitable form (e.g. gel, crystalline, amorphous, etc.), with adsorption of antigen to the salt being preferred. The concentration of $Al^{+++}$ in a composition for administration to a subject is preferably less than 5 mg/ml e.g. ≤4 mg/ml, ≤3 mg/ml, ≤2 mg/ml, ≤1 mg/ml, etc. A preferred range is between 0.3 and 1 mg/ml. A maximum of 0.85 mg/dose is preferred. Aluminium hydroxide and aluminium phosphate adjuvants are particularly suitable for use with the invention.

Compositions may include an antimicrobial, particularly when packaged in multiple dose format.

Antimicrobials such as thiomersal and 2-phenoxyethanol are commonly found in vaccines, but it is preferred to use either a mercury-free preservative or no preservative at all. The composition is preferably free of thiomersal.

Compositions may comprise detergent e.g. a TWEEN (polysorbate), such as TWEEN 80. Detergents are generally present at low levels e.g. <0.01% (v/v). Compositions may include residual detergent (e.g. deoxycholate) from OMV preparation. The amount of residual detergent is preferably less than 0.4 μg (more preferably less than 0.2 μg) for every μg of meningococcal protein.

If a vaccine includes lipooligosaccharide (LOS), the amount of LOS is preferably less than 0.12 μg (more preferably less than 0.05 μg) for every μg of protein.

Compositions may include sodium salts (e.g. sodium chloride) to give tonicity. A concentration of 10±2 mg/ml NaCl is typical e.g. about 9 mg/ml.

Vaccine Efficacy

Compositions for use in the present invention preferably have a vaccine efficacy against *N. gonorrhoeae* of at least 10% e.g. ≥20%, ≥30%, ≥40%, ≥50%, ≥60%, ≥70%, ≥80%, ≥85%, ≥90%, or more. As explained in reference 15, vaccination against gonorrhoea may be cost-effective even at a vaccine efficacy against *N. gonorrhoeae* as low as 20% (10% with a substantial increase in antibiotic resistant strains of *N. gonorrhoeae*).

Vaccine efficacy is determined by the reduction in relative risk of developing gonococcal disease in subjects who receive a composition according to the invention compared to subjects who do not receive such a composition (e.g. are non-immunized or who receive a placebo or negative control). Thus the incidence of gonococcal disease in a population which has been immunized according to the invention (e.g. 0.67% incidence) is compared to the incidence in a control population who has not been immunized according to the invention (e.g. 4.73% incidence) to give relative risk (e.g. 0.67/4.73=14%) and vaccine efficacy is 100% minus this figure (e.g. 86% efficacy).

Vaccine efficacy is determined for a population rather than for an individual. Thus it is a useful epidemiologic tool but does not predict individual protection. For instance, an individual subject might be exposed to a very large inoculum of the infecting agent, or might have other risk factors which make them more subject to infection, but this does not negate the validity or utility of the efficacy measure. The size of a population which is immunized according to the invention, and for which vaccine efficacy is measured, is ideally at least 100 and may be higher e.g. at least 500 subjects. The size of the control group should also be at least 100 e.g. at least 500.

Administration of the Composition

Compositions of the invention will generally be administered directly to a subject. Direct delivery may be accomplished by parenteral injection (e.g. subcutaneously, intraperitoneally, intravenously, intramuscularly, or to the interstitial space of a tissue), or by any other suitable route. Intramuscular administration is preferred e.g. to the thigh or the upper arm. Injection may be via a needle (e.g. a hypodermic needle), but needle-free injection may alternatively be used. A typical intramuscular dosage volume is 0.5 ml.

As used herein, a 'dose' of the composition is a volume of the composition suitable for administration to a subject as a single immunisation. Human vaccines are typically administered in a dosage volume of about 0.5 ml, although fractional doses may be administered (e.g., to children). The volume of the dose may further vary depending on the concentration of the antigens in the composition.

The composition may further be provided in a 'multidose' kit, i.e., a single container containing sufficient composition for multiple immunisations. Multidoses may include a preservative, or the multidose container may have an aseptic adaptor for removal of individual doses of the composition.

Administration can involve a single dose schedule, but will usually involve a multiple dose schedule. Preferably, a schedule of at least three doses is given. Suitable intervals between priming doses can be routinely determined e.g. between 4-16 weeks, such as one month or two months. BEXSERO® can be administered at ages of 2, 4 & 6 months, or at 2, 3 & 4 months, with a fourth optional dose at 12 months.

The subject who is immunized is a human being, who may be any age e.g. 0-12 months old, 1-5 years old, 5-18 years old, 18-55 years old, or more than 55 years old. Preferably, the subject who is immunized is an adolescent (e.g. 12-18 years old) or an adult (18 years or older).

Optionally, the subject is an adolescent or adult who has been immunized against *N. meningitidis* in childhood (e.g. before 12 years of age), and who receives a booster dose of an immunogenic composition according to the invention to protect against *N. gonorrhoeae*.

In a preferred embodiment, the subject who is immunized is at increased risk of infection with *N. gonorrhoeae* (e.g. at increased risk relative to the average risk in the general population). Such subjects may include (but are not limited to) those who are sexually active; those with multiple sexual partners (e.g. including sex workers); men who have sex with men (MSM); subjects with a partner who has tested positive for *N. gonorrhoeae*; military personnel; neonates/infants whose mother was positive for *N. gonorrhoeae* at birth (to protect against vertical transmission during delivery); and/or illegal drug users (reference 123 links illegal drug use before or during sex to increased risk of gonorrhoea).

In some embodiments, the subject who is immunized is already seropositive for *N. gonorrhoeae*. Recovery from infection with *N. gonorrhoeae* does not confer immunity against re-infection, and individuals may become infected multiple times, even with the same strain. Therefore, immunization of subjects seropositive for *N. gonorrhoeae* is of interest, for example to reduce the risk of re-infection.

Optionally, a subject who is immunized according to the invention is co-immunized against one or more additional sexually-transmitted infections, for example infections and/or diseases caused by human papillomavirus (HPV), hepatitis A virus, hepatitis B virus, human immunodeficiency virus (HIV), herpes simplex virus (HSV), *Chlamydia trachomatis* and/orZika virus. In a preferred embodiment, the subject is co-immunized against *N. gonorrhoeae* and HPV. This embodiment is particularly preferred for immunization of adolescents, especially adolescent females. Preferably, the subject is immunized against HPV types 16 and 18 (e.g. using the CERVARIX® vaccine). Optionally the subject is also immunized against HPV types 6 and 11 (e.g. using the GARDASIL® vaccine). The subject may also be immunized against HPV types 31, 33, 45, 52 and 58 (e.g. using the GARDASIL® 9 vaccine). Such a co-immunization strategy is particularly suitable for adolescent subjects.

Where the invention refers to co-immunization, the different immunogenic compositions/vaccines can be administered either separately or as a combination.

Where the vaccines are administered separately, they will typically be administered at different sites e.g. one vaccine to the left upper arm, and a second vaccine to the right upper arm. Thus two vaccines may be administered contralaterally (e.g. both arms, or both legs, or a contralateral arm and leg) or ipsilaterally (e.g. the arm and leg on the same side of the body). Although the vaccines are administered separately, they are administered at substantially the same time (e.g. during the same medical consultation or visit to a healthcare professional or vaccination centre), such as within 1 hour of each other.

Rather than co-immunising separately, however, administration as a combination may be performed. Thus co-immunisation may use a combination vaccine i.e. a single composition in which the different immunogens are admixed. Combination vaccines offer subjects the advantage of receiving a reduced number of injections, which can lead to the clinical advantage of increased compliance.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 124-130, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±100%.

Where the invention concerns an "epitope", this epitope may be a B-cell epitope and/or a T-cell epitope, but will usually be a B-cell epitope. Such epitopes can be identified empirically (e.g. using PEPSCAN [131,132] or similar methods), or they can be predicted (e.g. using the Jameson-Wolf antigenic index [133], matrix-based approaches [134], MAPITOPE [135], TEPITOPE [136,137], neural networks [138], OptiMer & EpiMer [139, 140], ADEPT [141], Tsites [142], hydrophilicity [143], antigenic index [144] or the methods disclosed in references 145-149, etc.). Epitopes are the parts of an antigen that are recognized by and bind to the antigen binding sites of antibodies or T-cell receptors, and they may also be referred to as "antigenic determinants".

References to a percentage sequence identity between two amino acid sequences means that, when aligned, that percentage of amino acids are the same in comparing the two sequences. This alignment and % homology or sequence identity can be determined using software programs known in the art, for example those described in section 7.7.18 of ref. 150. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 151.

The word "substantially" does not exclude "completely" e.g. a composition which is "substantially free" from Y may be completely free from Y. Where necessary, the word "substantially" may be omitted from the definition of the invention.

Throughout this document, and in particular in the Examples section below, references to "rMenB" refer to the recombinant *meningitidis* B protein antigens present in the BEXSERO® vaccine product, i.e. the antigenic components excluding the OMV component.

EXAMPLES

In the following Examples all references to 287 (NHBA) refer to the AG variant.

Example 1—*N. meningitidis* NHBA Induces Antibodies with Bactericidal Activity Against *N. gonorrhoeae*

To evaluate whether antibodies elicited by meningococcal NHBA are able to confer protection against *N. gonorrhoeae*, mice were immunized three times with meningococcal NHBA in combination with Alum hydroxide or Freund's Adjuvant (see General Methods for full details). Mice were bled before the first immunization and two weeks after the third dose, and the antisera were tested for their ability to induce complement-mediated killing of *N. gonorrhoeae* F62 strain.

In all experiments performed meningococcal NHBA antiserum showed bactericidal activity against F62 strain in the presence of human complement. Similar results were obtained using FCA or Alum formulations. No bactericidal activity was detected when serum against negative control antigens (protein 919 or 726) or pre-imnmune sera were used (Table 1).

TABLE 1

Bactericidal activity of sera raised against *N. meningitidis* ΔG287 antigen on *N. gonorrhoeae* F62 strain

| ANTIGEN | scheme | adjuvant | hSBA Titer on F62 | |
|---|---|---|---|---|
| | | | Pre | Post 3 |
| negative controls | | | | |
| 726 citopl. | 74-5 | FCA | | <10 |
| 919 | 70-1 | — | | <10 |
| ΔG287 KA | 131-3 | Al(OH)$_3$ | | 10 |
| " | 136-16 | Al(OH)$_3$ | | 400 |
| ΔG287-HIS | 120-14 | FCA | | 100 |
| " | 137-5 | Al(OH)$_3$ | | 100 |
| " | 124-8 | Al(OH)3 | <50 | >200 |
| ΔG287-HIS | 116-4 | FCA | <50 | 100 |
| ΔG287-HIS | 147-5 | FCA | <200 | 1600 |
| ΔG287-953 | 98-4 | FCA | | 100 |
| " | 116-1 | FCA | | 100 |
| " | 116-5 | Al(OH)$_3$ | | 100 |
| " | 131-2 | Al(OH)$_3$ | | 100 |
| " | 135-6 | Al(OH)$_3$ | | 100 |
| " | 136-7 | Al(OH)$_3$ | | 10 |
| " | 137-1 | Al(OH)$_3$ | | 100 |

In BEXSERO® NHBA is fused to *N. meningitidis* antigen 953 (ΔG287-953)(SEQ ID NO:9). To evaluate whether the meningococcus vaccine is able to confer protection also against *N. gonorrhoeae*, the bactericidal activity of sera raised against the fusion protein ΔG287-953 was tested.

As shown in Table 1, anti-ΔG287-953 sera were able to kill *N. gonorrhoeae* F62 strain in the presence of human complement when the antigen was administered in combination with FCA as well as when Al(OH)$_3$ was used as adjuvant.

These data suggest a possible cross protection induced by BEXSERO® against *N. gonorrhoeae*.

We also investigated whether the homologue of NHBA in gonococcus (ΔG287NG) was able to elicit functional antibodies. Sera of mice immunized three times with gonococcal ΔG287NG (SEQ ID NO:15) showed bactericidal activity against both *N. meningitidis* and *N. gonorrhoeae*. Similar results were observed for the antigen formulated with FCA or Alum as adjuvant (Table 2).

TABLE 2

Bactericidal activity of sera raised against *N. gonorrhoeae*
ΔG287NG antigen on *N. meningitidis* group B 2996
strain and on *N. gonorrhoeae* F62 strain.

| ANTIGEN | scheme | adjuvant | rSBA Titer on 2996 | hSEA Titer on F62 Pre | hSEA Titer on F62 Post 3 |
|---|---|---|---|---|---|
| ΔG287NG-his | 144-2 | FCA | 128 (50%) | <50 | 200 |
| " | 154-12 | FCA | 256 | <200 | 200 |
| " | 144-1 | Al(OH)3 | <4 | <50 | 200 |
| " | 154-11 | Al(OH)3 | 256 | 200 | 800 |

Example 2—Antibodies Elicited by NHBA Recognize *N. gonorrhoeae* and Activate the Complement Cascade NHBA is a surface exposed protein in *N. meningitidis*. To evaluate whether the homologous protein is also present on the surface of *N. gonorrhoeae*, FACS analysis was performed on F62 gonococcus strain using anti-ΔG287NG (gonococcal) antisera. Bacteria incubated with immune sera showed a shift in the fluorescence compared to the pre-immune serum, suggesting that the protein is expressed on the surface of gonococcus. No significant differences were observed between FCA (FIG. 1A) and Alum formulations (FIG. 1B).

Also the antiserum raised against the *N. meningitidis* NHBA was tested and similar results were obtained (see FIG. 2B compared to negative control shown in FIG. 2A), demonstrating that the NHBA from meningococcus is able to induce cross-reactive antibodies.

Figure 2A:
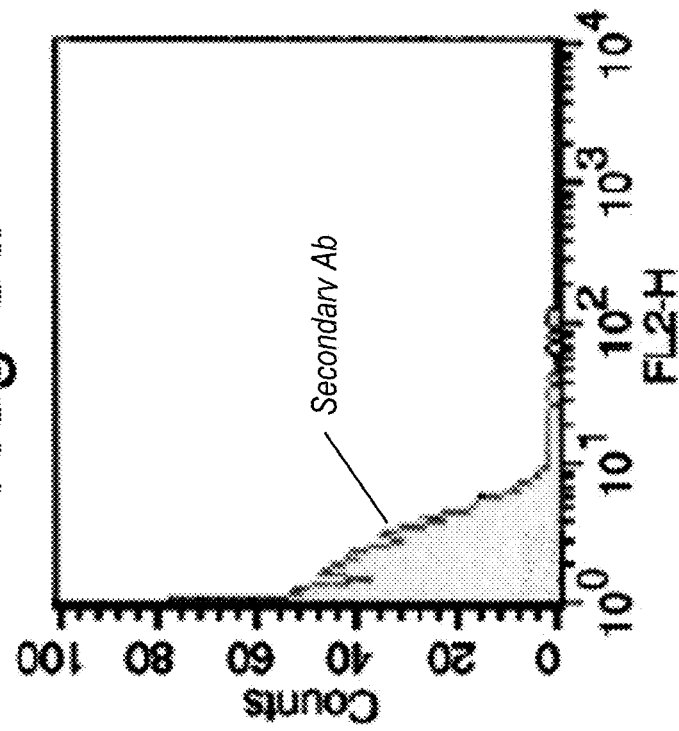
Figure 2C:
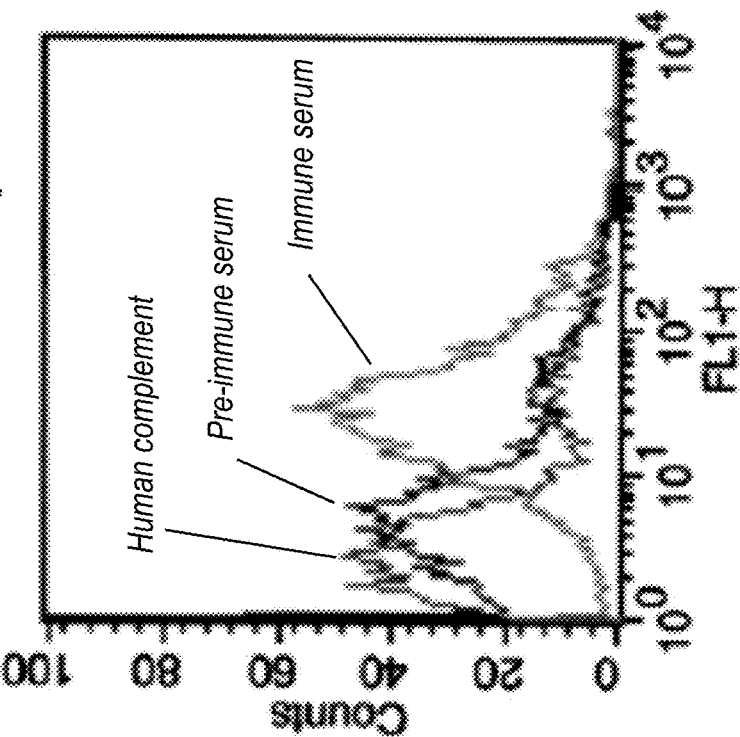
Figure 2D:
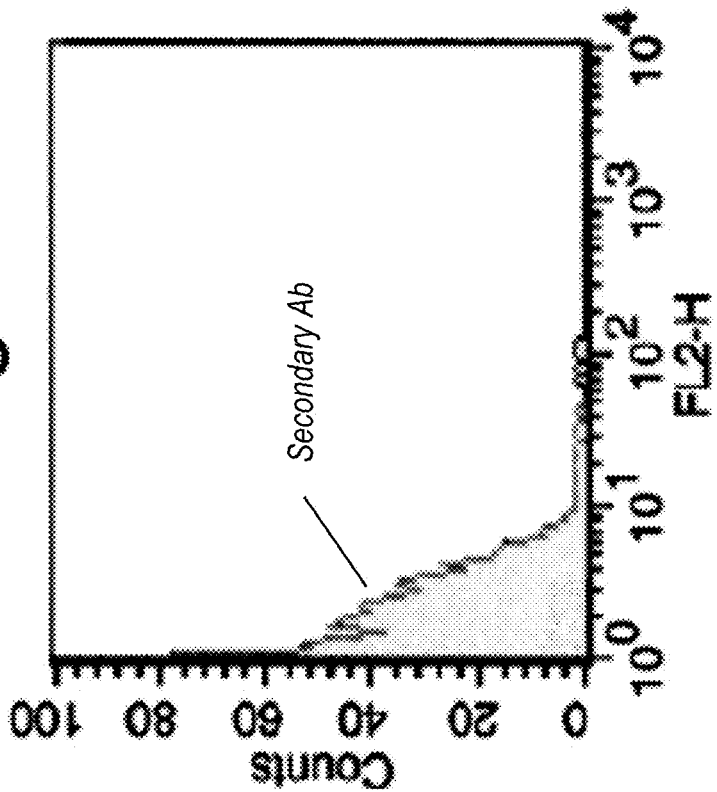

Moreover, in the presence of human complement, C3 deposition was observed on the surface of gonococcus, suggesting the activation of complement cascade triggered by anti-ΔG287 antibodies (see FIG. 2D, compared to negative control shown in FIG. 2C). No C3 deposition was observed when bacteria were incubated with complement alone.

As negative controls, bacteria were incubated with the secondary antibody alone (anti-mouse IgG PE-conjugated or anti-human C3c FITC-conjugated respectively) (FIGS. 2A and 2C).

Figure 3B:
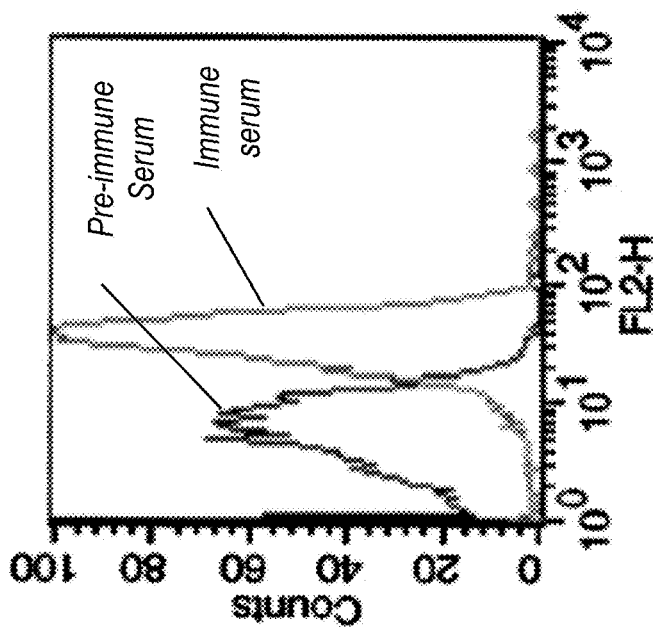
FIG. 3A-3D—Anti-*N. meningitidis* 287-953 antisera recognize *N. gonorrhoeae* F62 strain (FIG. 3A, antisera raised using FCA adjuvant.
Figure 3A:
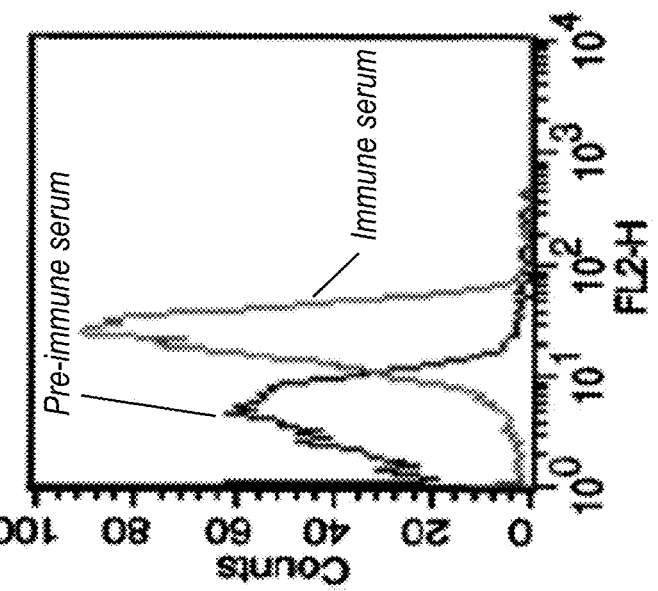
Figure 3C:
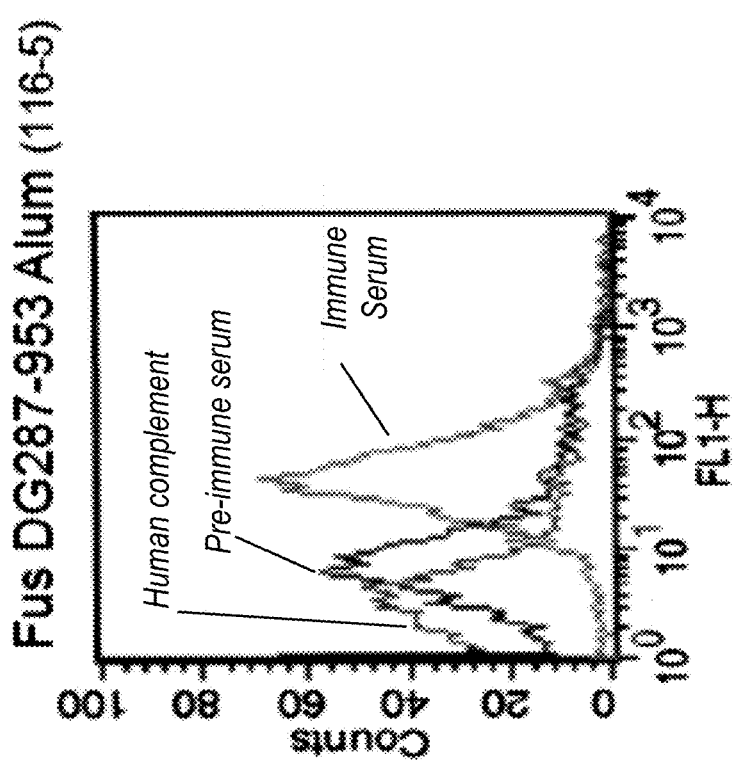
Figure 3D:
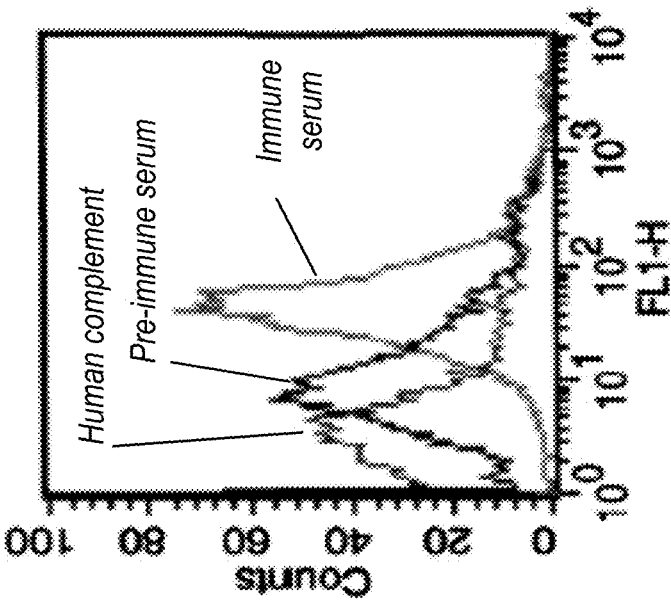

Similar results were observed with the antiserum against ΔG287-953 with no major differences when FCA (FIG. 3A and FIG. 3C) or Alum (FIG. 3B and FIG. 3D) were used as adjuvant.

All these data are in agreement with the bactericidal activity showed in Tables 1 and 2.

In conclusion, *N. meningitidis* NHBA is able to induce cross-functional antibodies that recognize *N. gonorrhoeae*, activate the complement cascade and mediate bacteria killing. This study provides a rationale for the use of the individual antigens in BEXSERO® in immunizing against *N. gonorrhoeae*.

General Methods Used for Examples 1 and 2

Animals and Immunization Protocol

Six-week-old female CD1 mice were immunized with 20 μg of protein intraperitoneally on day 1, 21 and 35. Antigens were adsorbed to Al(OH)$_3$ or given together with Complete Freund's Adjuvant for the first dose and incomplete Freund's adjuvant for the second and third booster doses. Blood samples were collected two weeks after the last dose and used for serological analysis.

FACS and C3 Binding

*N. gonorrhoeae* F62 strain was grown in GC medium supplemented with 1% isovitalex from O.D.$_{600}$=0.1 up to O.D.$_{600}$=0.3. After centrifugation the bacteria were resuspended in Hank's Balanced Salt Solution plus 1 mM CaCl$_2$ and 0.15 mM MgClz (HBSS++). 100 μl/well of bacteria were seeded in a 96-well plate, centrifuged, resuspended with mouse serum diluted in HBSS++ and incubated for 15-30 min at 37° C.

For the C3 binding assay the incubation of bacteria with mouse serum was carried out in the presence of human serum as complement source at final concentration of 10%. Human serum to be used as the complement source was previously adsorbed to *N. gonorrhoeae*.

Antibody binding was detected using, as secondary antibody, an anti-mouse IgG FITC-conjugated antibody diluted 1:100 or an anti-mouse PE-conjugated antibody diluted 1:200 in HBSS++.

The complement deposition was detected using an anti-human C3c FITC-conjugated antibody diluted 1:50 in HBSS++.

After 20 min incubation at 37° C. with the secondary antibodies, bacteria were fixed with para-formaldehyde and the fluorescence was determined by FACS.

Bactericidal Activity

Gonococcus F62 strain was grown in GC medium supplemented with 1% isovitalex for 1.5 hrs from O.D.$_{600}$=0.1 up to O.D.$_{600}$=0.3. The bacteria were diluted to obtain an O.D.$_{600}$=0.1, again diluted 1:10 and incubated 1 hr at 37° C. with the following reaction mix: 125 μl of diluted bacteria, 25 μl of *N. gonorrhoeae*-adsorbed human serum as exogenous complement source, 25 μl of serum at the desired concentration and 75 μl of 5% BSA in HBSS. The reaction mix was diluted and bacteria were plated on a GC+1% isovitalex-plate at time 0 and after 1 hr of incubation at 37° C. Colonies were counted after 18 hrs of growth at 37° C. in 5% CO$_2$.

Serum bactericidal titers were defined as the serum dilution resulting in 50% decrease in CFU after incubation of bacteria with reaction mixture compared to control CFU at time zero.

*N. meningitidis* was grown overnight at 37° C. on chocolate agar plates (starting from a frozen stock) with 5% C02. Colonies were collected and used to inoculate 7 ml Mueller Hinton broth, containing 0.25% glucose, to reach an OD$_{600}$ of 0.05-0.06. The culture was incubated for approximately 1.5 hours at 37° C. with 5% C02 with shaking until the OD$_{600}$ reached the value of 0.24-0.25. Bacteria were diluted in GBSS buffer (Gey's balanced salt solution—SIGMA cat. G9779) and 1% (w/v) BSA (assay buffer) at the working dilution 1:10000 (10$^5$ CFU/ml). The total volume of the final reaction mixture was 50 μl with 25 μl of serial two fold dilution of test serum, 12.5 μl of bacteria at the working dilution, 12.5 μl of baby rabbit complement (final concentration 25%).

Controls included bacteria incubated with complement serum, immune sera incubated with bacteria and with complement inactivated by heating at 56° C. for 30 min. Immediately after the addition of the baby rabbit complement, 10 μl of the controls were plated on Mueller-Hinton agar plates using the tilt method (time 0). The 96-well plate was incubated for 1 hour at 37° C. with 5% CO$_2$ with rotation. 7 μl of each sample was plated on Mueller-Hinton agar plates as spots, whereas 10 μl of the controls were plated on Mueller-Hinton agar plates using the tilt method (time 1). Agar plates were incubated for 18 hours at 37° C. with 5% $CO_2$ and the colonies corresponding to time 0 and time 60 were counted.

The data were used to calculate the reciprocal serum dilution at which 50% of the bacteria are killed (50% titer).

Example 3—BEXSERO® Vaccine Composition, OMVnz, and rMenB Protein Antigens Induce Antibodies that are Bactericidal Against FA1090

Animals and Immunization Protocol

Six-week-old female CDI mice (10 animals/group) were immunized with BEXSERO® (1:2.5 human dose corresponding to 20 µg of protein antigen and 10 µg of OMV), or OMVnz (10 µg) or recombinant MenB protein antigen (rMenB) (20 sg each) in combination with an alum adjuvant intraperitoneally on day 1, 21 and 35. Adjuvant alone and an unrelated antigen (protein F from Respiratory Syncytial Virus (RSV)) were used as negative controls. Sera samples were collected before the first immunization and two weeks after the last dose and used for serological analysis.

Bactericidal Activity

Gonococcus strain FA1090 was grown in GC medium supplemented with 1% isovitalex for 1.5 hrs from $O.D._{600} \cong 0.1$ up to $O.D._{600} \cong 0.3$. The bacteria were diluted with a suspension of sera in SBA buffer (dPBS, 0.1% glucose, 1% BSA) and incubated for 1 hr at 37° C. with sera to be tested in the presence of human serum as exogenous complement source (16% v/v). Bacteria were then plated on a GC+1% isovitalex-plate.

Colonies were counted after 18 hrs of growth at 37° C. in 5% $CO_2$.

Serum bactericidal titers were calculated as the reciprocal dilution resulting in 50% killing with respect to the control (bacteria plus complement).

Results

Figure 4:
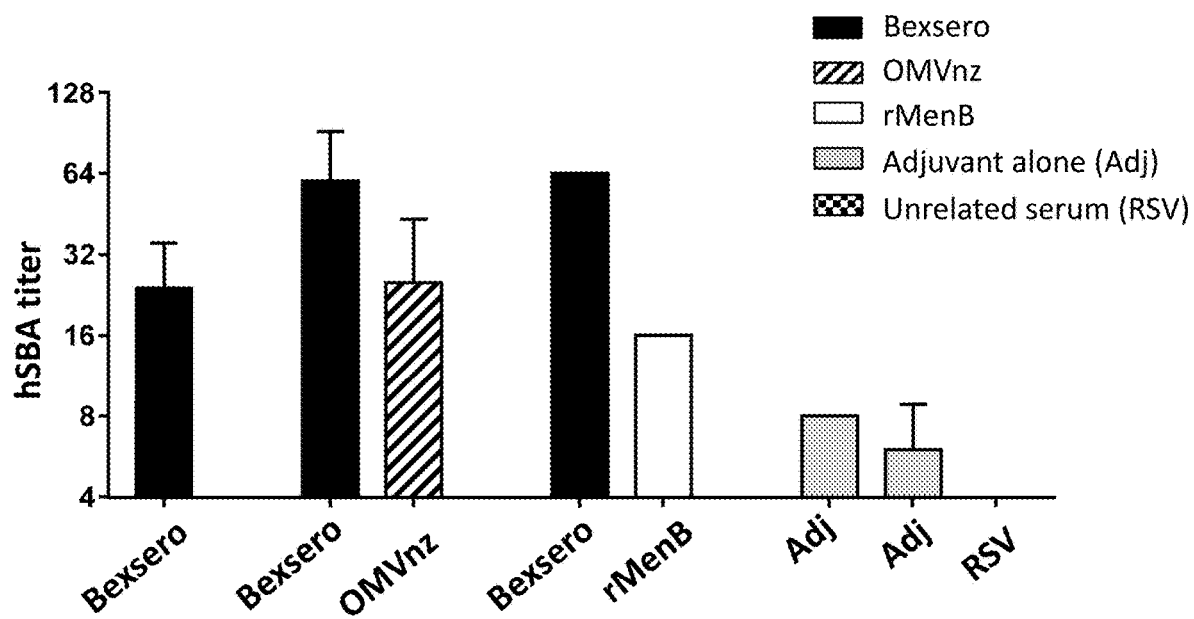
FIG. 4—SBA assay shows BEXSERO®, OMVnz and protein antigen components of BEXSERO® induce bactericidal antibodies against *N. gonorrhoeae* FA1090 strain.

As can be seen from FIG. 4, the hSBA titre of pool of sera from mice immunized with BEXSERO®, OMVnz and rMenB is high ($\geq 16$), in each if the three immunization schemes represented showing bactericidal activity of the sera raised against each of BEXSERO®, OMVnz and rMenB against *N. gonorrhoeae*. In contrast, the titre of the adjuvant alone is low ($\leq 8$ in two different immunization schemes) and does not reach the threshold level for a statistically meaningful (i.e. non-background) titre for bactericidal activity. The measured hSBA titre for RSV is below 4, the lowest serum dilution tested, and is not shown on the graph.

Figure 5A:
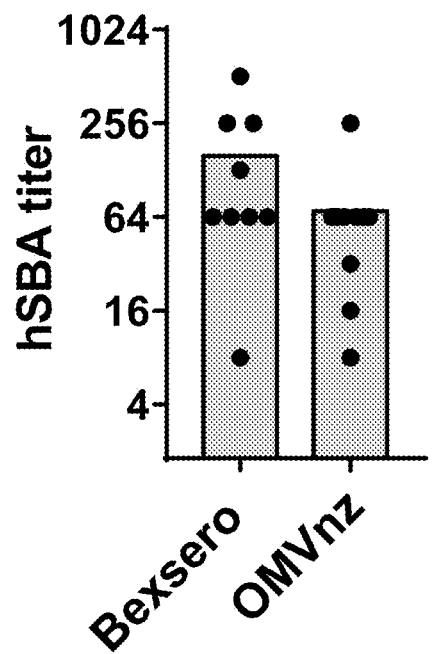
FIG. 5A-5B—Graphs the hSBA titre measured in sera from mice immunized with BEXSERO® or OMVnz, with each dot representing the result from an individual mouse (FIG. 5A), and the percentage of mice producing serum having a Hsba titre of ≥32 (FIG. 5B).
Figure 5B:
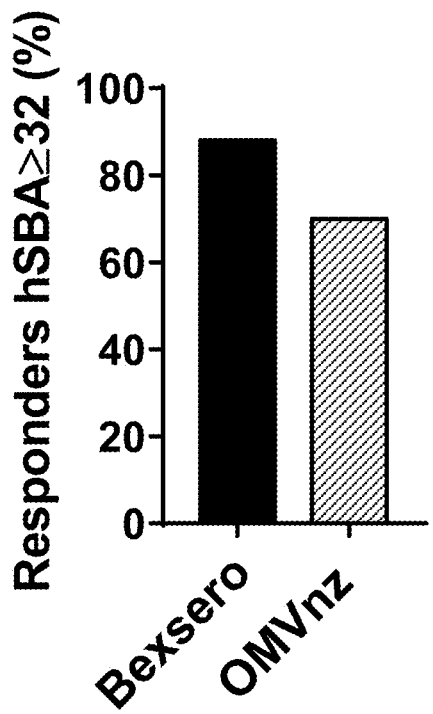

As shown in FIGS. 5A and 5B, the pool analysis of hSBA of sera from mice immunized with BEXSERO®, OMVnz presented in FIG. 4 is confirmed by considering hSBA for single mice within the pooled population.

FIG. 5A plots the hSBA titre measured using the serum of each of the mice immunized with BEXSERO® or OMVnz, with each dot representing the result for immune serum from an individual mouse. These data show that the BEXSERO® and OMVnz are able to induce a homogenous bactericidal response against *N. gonorrhoeae*. As shown in FIG. 5B, a high percentage of the mice immunized with BEXSERO® ($\geq 80\%$) or OMVnz ($\geq 70\%$) produced immune serum having a high hSBA titre of $\geq 32$, indicating a strong bactericidal antibody response against *N. gonorrhoeae*.

Figure 6:
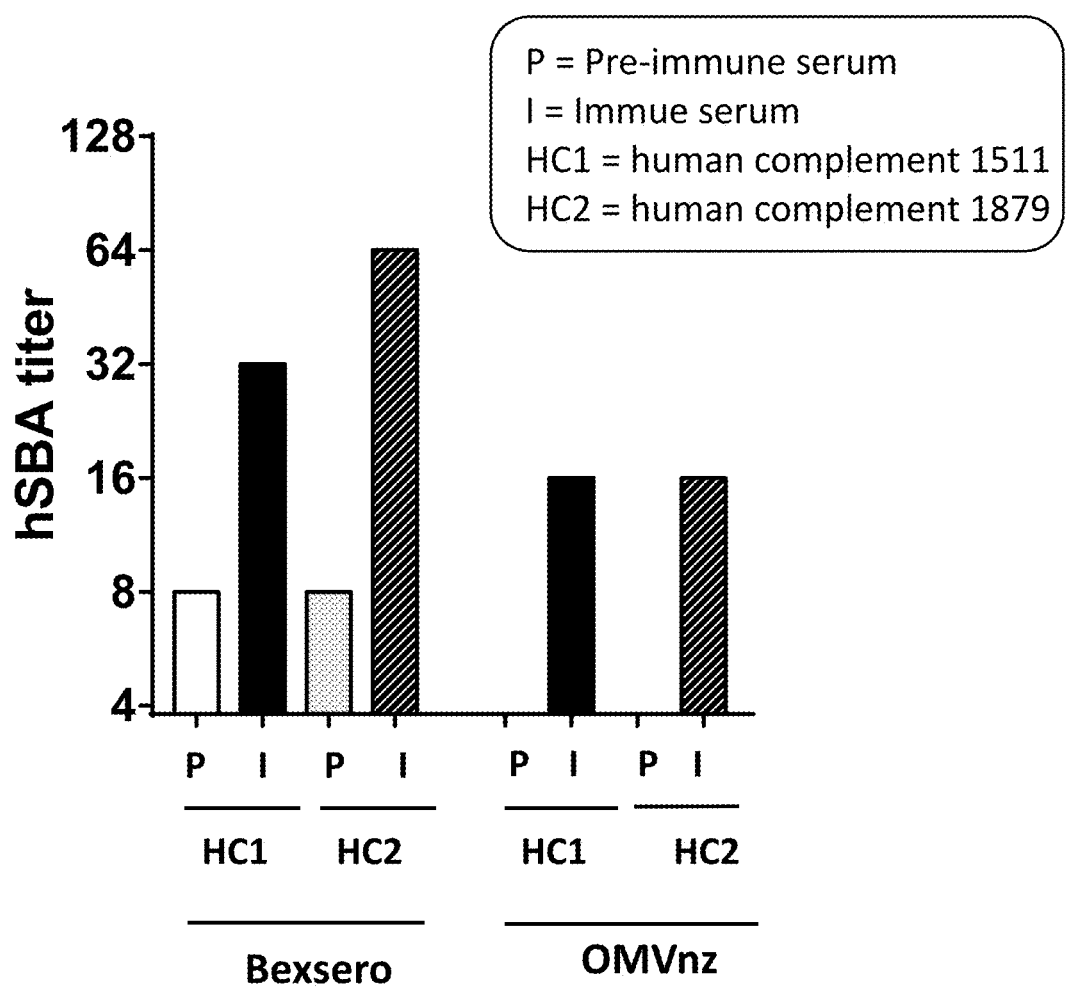
FIG. 6—Graph showing that results illustrated in FIGS. 4, 5A and 5B are confirmed with different human complement lots (HC1511 and HC1879).

The positive hSBA results for anti-BEXSERO® sera and anti-OMVnz sera against *N. gonorrhoeae* shown in FIGS. 4 and 5A and 5B are further supported using different complement lots to reflect the variation in human complement, and these results are shown in FIG. 6. Two different human complement (HC) lots were tested—HC 1511 and HC 1879—using pre-immune (P) and immune (I) serum samples.

In each of the BEXSERO® assays the result observed for the pre-immune serum (i.e. pooled serum collected from the mice prior to immunization with BEXSERO®) was $\leq 8$ and so does not reach the threshold level for a statistically meaningful (i.e. non-background) titre for bactericidal activity. In each of the OMVnz assays no bactericidal activity was observed using pre-immune serum. In contrast, the hSBA titres using immune serum from mice immunized with BEXSERO® or OMVnz (i.e. serum collected from the mice following immunization) was positive in each immunization scheme (a titre of $\geq 16$). The results for mice immunized with BEXSERO® are particularly strong for both of the human complements tested, with SBA titres of 32 for HC 1511 and 64 for HC1879). The results for mice immunized with OMVnz are consistent (antibody titre of 16) for both HC 1511 and HC 1879.

Competitive SBA

The results observed in the hSBA assays were reinforced by carrying out a competitive SBA assay to provide further indirect evidence of the immunogenic activity of BEXSERO®, OMVnz and rMenB against *N. gonorrhoeae*.

Figure 7:
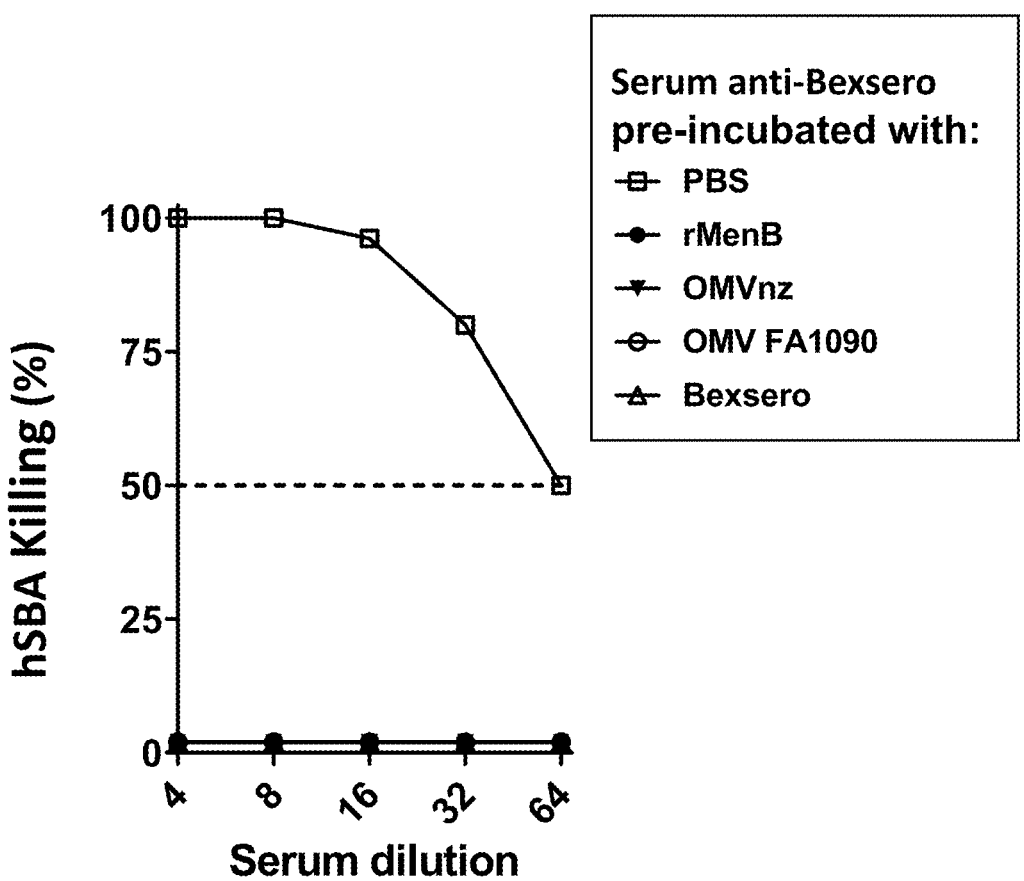
FIG. 7—Competitive hSBA indicates BEXSERO®, OMVnz and protein antigen components of BEXSERO® induce bactericidal antibodies against *N. gonorrhoeae* FA1090 strain, and the SBA activity of anti-BEXSERO® serum is specific.

Pooled serum from mice immunized with BEXSERO® was pre-incubated with either (i) PBS (phosphate-buffered saline) as a negative control. (ii) rMenB, (iii) OMVnz, (iv) OMV from gonococcal strain FA1090 as a further control, or (v) BEXSERO®. The sera were subsequently incubated with target gonococci bacteria in the presence of human complement. Killing of the bacteria was then assessed, and the results are shown in FIG. 7.

As can be seen in the graph, killing was abolished when the anti-BEXSERO® immune sera was pre-incubated with BEXSERO®, rMenB, OMVnz and OMV FA1090, because bactericidal antibodies in the recipients' sera bind to the antigens in these compositions during the pre-incubation phase and are therefore not available to bind to surface antigens on the bacteria. In contrast, pre-incubation with PBS has no effect on the bactericidal activity of immune sera, because PBS does not bind to the antibodies raised in the immune sera and said antibodies are therefore available to bind to the target bacterial surface antigens and initiate killing.

The competitive hSBA results demonstrate the specificity of the bactericidal antibodies, validate the hSBA results for BEXSERO®, rMenB and OMVnz described above and further support the immunogenicity of BEXSERO® and its component antigens against *N. gonorrhoeae*.

Example 4—Sera Against BEXSERO® Reduces Adhesion of FA1090 to Human Cervical ME180 Cells In the absence of a suitable correlate of protection for gonorrhoea, the inventors performed a bacterial adhesion inhibition assay to test whether antibodies produced by BEXSERO® can prevent gonococci from adhering to cells of a human cervical cell line (ME180).

Figure 8:
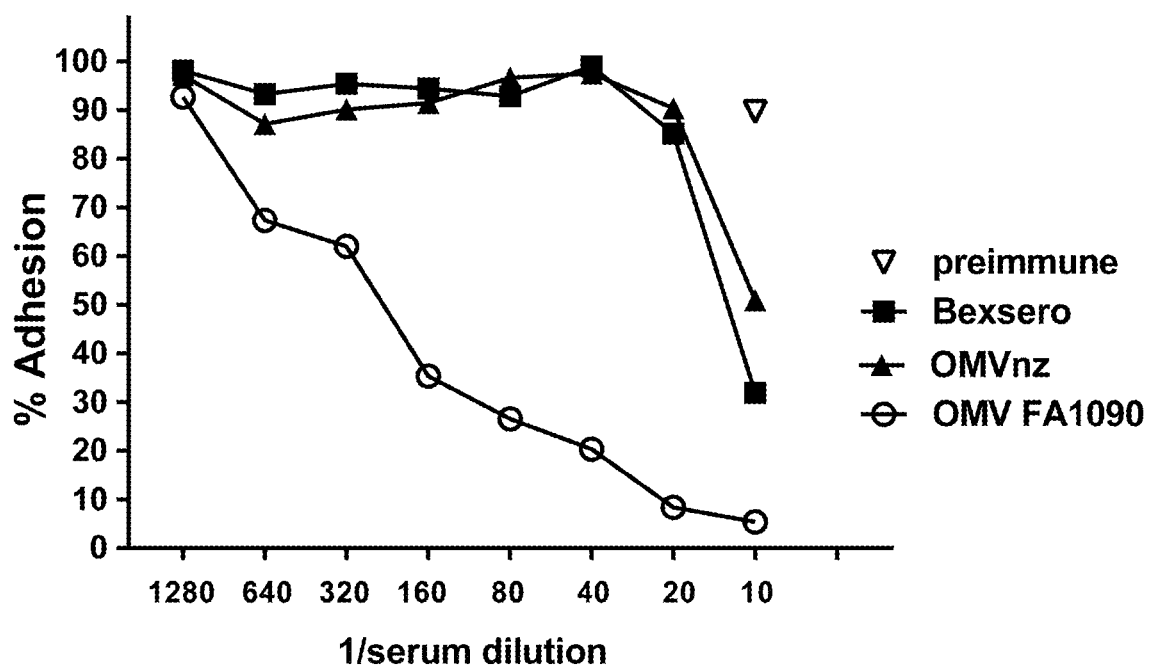
FIG. 8—Bacterial adhesion inhibition assay shows sera raised against BEXSERO®, OMVnz and OMV FA1090 reduce adhesion of FA1090 to human cervical ME180 cells.

Bacteria from gonococcal strain FA1090 were labelled with a fluorescent dye (OREGON GREEN® 488, Thermofisher) and the labelled bacteria were pre-incubated for 1 hour with serially diluted sera obtained from mice immunized with BEXSERO®, OMVnz or OMV FA1090 or with a preimmune serum. Cells from human epithelial cervical cell line ME180 were then infected for 1 hour with strain FA1090 bacteria+sera to allow for adhesion of the bacteria to the epithelial cells. In a final step, the plate was washed to remove unbound bacteria and fluorescent output was measured. Fluorescent output is proportional to bacterial adhesion to the epithelial cells, meaning that a decrease in fluorescence compare to control (bacteria plus cells without serum) corresponds to a decrease in adhesion of labelled gonococci to the cells. As shown in FIG. 8, sera against Bexsero® and OMVnz at high concentration (1/10 dilution) reduces the adhesion of gonococcus FAI1090 to human cervical ME180 cells, which is an interesting and important result in a clinical context. Sera against OMV FA1090 (i.e. homologous sera) reduced adhesion at much lower concentrations No significant reduction in adhesion was observed in the pre-immune serum.

Example 5—Meningococcal NHBA Induces Antibodies that am Bactericidal Against FA1090 Animals and Immunization Protocol Six-week-old female CD1 mice (10 animals/group) were immunized with 20 μg of protein (287-953 or 287 in combination with an alum adjuvant intraperitoneally on day 1, 21 and 35. An unrelated antigen, protein F from Respiratory Syncytial Virus (RSV), was used as a negative control. Sera samples were collected before the first immunization and two weeks after the last dose and used for serological analysis.

Bacteridid Activity

Gonococcus strain FA1090 was grown in GC medium supplemented with 1% isovitalex for 1.5 hrs from $O.D._{600}=0.1$ up to $O.D._{600}=0.3$. The bacteria were diluted with a suspension of sera in SBA buffer (dPBS, 0.1% glucose, 1% BSA) and incubated for 1 hr at 37° C. with sera to be tested in the presence of rabbit complement (5% v/v). Bacteria were then plated on a GC+1% isovitalex-plate.

Colonies were counted after 18 hrs of growth at 37° C. in 5% $CO_2$.

Serum bactericidal titers were calculated as the reciprocal dilution resulting in 50% killing with respect to the control (bacteria plus complement).

Figure 9:
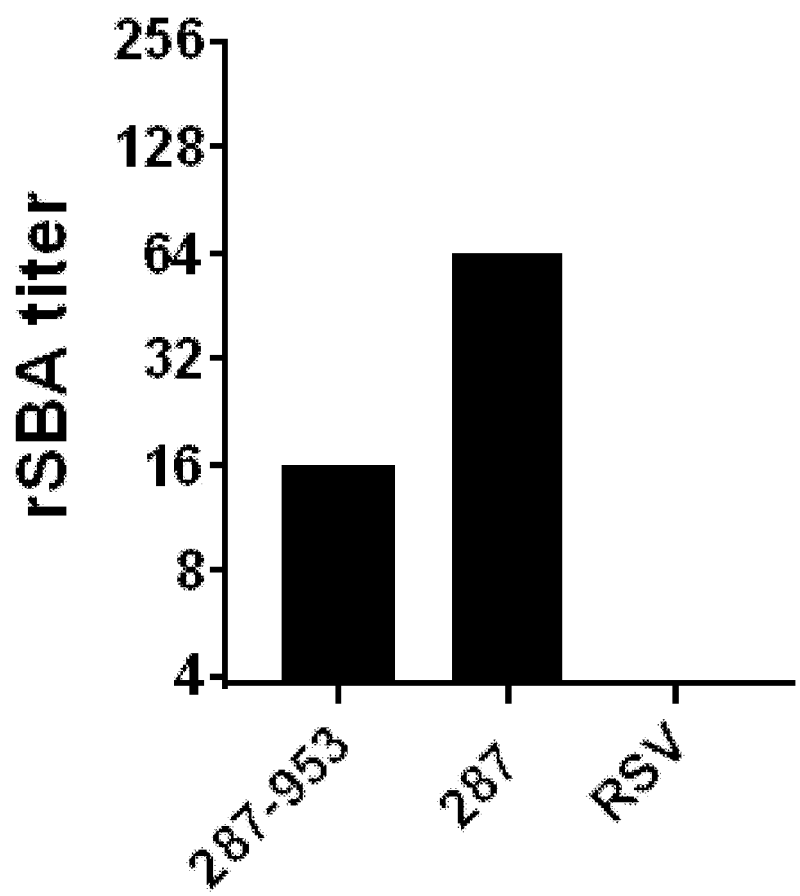
FIG. 9—Graph showing SBA results for 287-953 (NHBA-GNA1030 fusion), 287 (NHBA antigen alone), and a negative control (RSV) using 5% rabbit complement.

As can be seen from the rSBA titres in FIG. 9, both the 287 anti-serum and 287-953 fusion anti-serum showed bactericidal activity against FA1090 strain in the presence of rabbit complement. This is in contrast to the control RSV anti-serum, which produced an rSBA titre below the threshold level for bactericidal activity.

Figure 10:
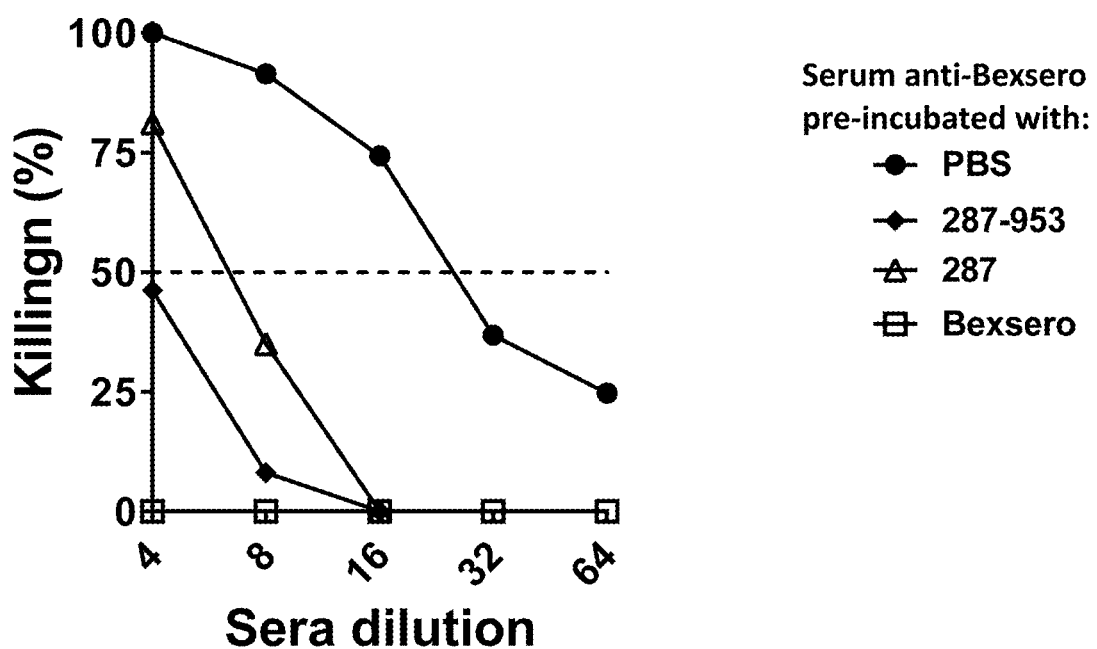
FIG. 10—Competitive hSBA showing that BEXSERO®, 287 and 287-953 induce bactericidal antibodies, and confirming that the SBA activity of anti-BEXSERO® serum is specific.

FIG. 10 shows the results of a competitive SBA in which anti-BEXSERO® serum was pre-incubated with BEXSERO®, 287-953, 287 and PBS (as a negative control) in the presence of human complement. These data show that BEXSERO®, 287 and 287-953 abolish the activity of bactericidal antibodies in the anti-BEXSERO® serum. This is in contrast to the result for the PBS control, wherein bactericidal killing is maintained above the 50% threshold until the sera dilution reaches 1/32 with no effect on the bactericidal activity of the immune sera.

Example 6—Meningococcal Accessory Proteins 953 (GNA1030) and 936 (GNA2091) Induce Antibodies that are Bactericidal Against FA1090

Six-week-old female CD1 mice (10 animals/group) were immunized with 20 μg of protein (either 953, 936-741v1.1 fusion, or 741v1.1) in combination with an alum adjuvant intraperitoneally on day 1, 21 and 35. Adjuvant alone was used as negative control. Sera samples were collected before the first immunization and two weeks after the last dose and used for serological analysis.

Bactericidal Activity

Gonococcus strain FAI090 was grown in GC medium supplemented with 1% isovitalex for 1.5 hrs from $O.D._{600}\cong0.1$ up to $O.D._{600}\cong0.3$. The bacteria were diluted with a suspension of sera in SBA buffer (dPBS, 0.1% glucose, 1% BSA) and incubated for 1 hr at 37° C. with sera to be tested in the presence of human serum as exogenous complement source (16% v/v). Bacteria were then plated on a GC+1% isovitalex-plate.

Colonies were counted after 18 hrs of growth at 37° C. in 5% $CO_2$.

Serum bactericidal titers were calculated as the reciprocal dilution resulting in 50% killing with respect to the control (bacteria plus complement).

Results

Figure 11:
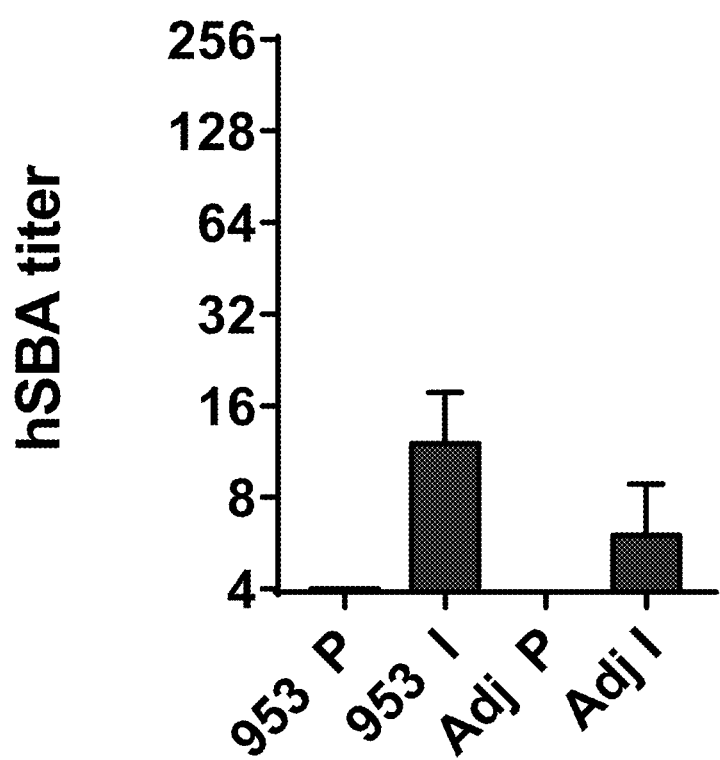
FIG. 11—Graph showing hSBA results for accessory protein 953 (GNA1030) and an adjuvant control. Assays conducted using pre-immune serum (P) and immue serum (I).

As can be seen from FIG. 11, in the hSBA assay anti-953 immune sera was able to induce bactericidal antibodies against gonococcus strain FA1090, with antibody titres >8. In contrast, neither sera immunized with adjuvant alone nor either of the pre-immune sera were able to induce statistically meaningful titres of bactericidal antibodies against FA1090.

Figure 12A:
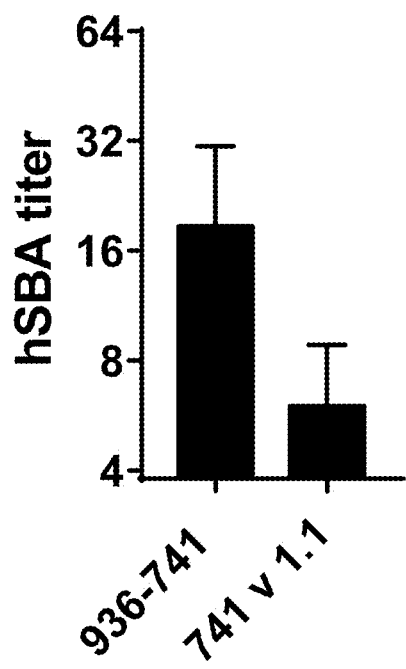
FIGS. 12A and 12B—FIG. 12A graphs hSBA results for 936-741 (GNA2091-fHbp v1.1 fusion) and for fHbp v1.1 alone.

FIG. 12A shows that the hSBA titre of bactericidal antibodies induced by anti-936-741 (GNA2091-fHbp v1.1 fusion) sera is significant (>16) and far higher than the titre induced by anti-741 (fHbp v1.1) sera. This indicates that it is the presence of the 936 antigen in the 936-741 fusion that is responsible for inducing antibodies that are bactericidal against FA1090.

Figure 12B:
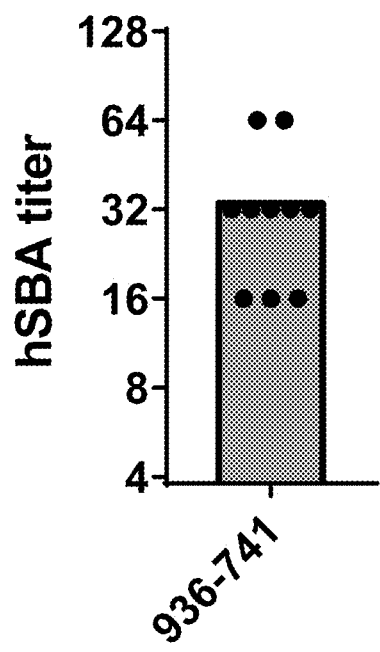

The result for the 936-741 fusion is further explored in FIG. 12B, which plots the hSBA titre measured using the serum of each of the mice immunized with 936-741, with each dot representing the result for immune serum from an individual mouse. These data show that the 936-741 fusion antigen is able to induce a homogenous bactericidal response against N. gonorrhoeae, with the majority of the individual results (7 out of 10) producing a SBA titre of ≥32, indicating a strong bactericidal antibody response against N. gonorrhoeae.

Competitive hSBA

The results observed in the hSBA assays were reinforced by carrying out a competitive SBA assay to provide further indirect evidence of the immunogenic activity of the 936 accessory protein against N. gonorrhoeae.

Figure 13:
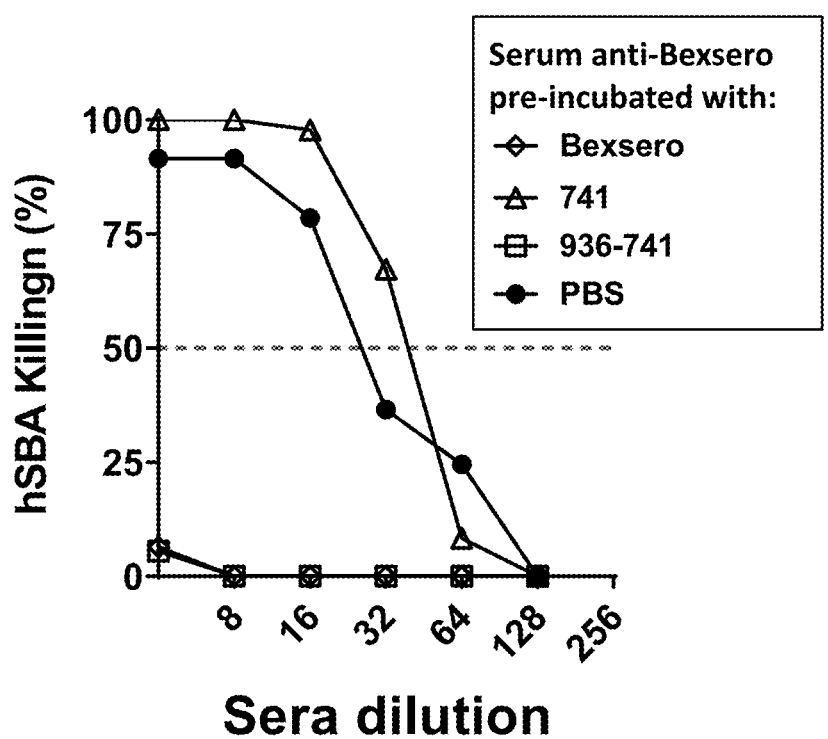
FIG. 13—Competitive hSBA showing that BEXSERO® and 936-741 induce bactericidal antibodies, and confirming that the SBA activity of anti-BEXSERO® serum is specific.

Sera from recipients who had been immunized with BEXSERO® was pre-incubated with either (i) PBS (phosphate-buffered saline) as a negative control, (ii) BEXSERO®, (iii) 741 alone, or (iv) the 936-741 fusion. The sera were subsequently incubated with target gonococci bacteria in the presence of human complement. Killing of the bacteria was then assessed, and the results are shown in FIG. 13.

As can be seen in the graph, killing was abolished when the anti-BEXSERO® immune sera was pre-incubated with either BEXSERO® or the 936-741 fusion, because bactericidal antibodies in the recipients' sera bind to the antigens in these compositions during the pre-incubation phase and are therefore not available to bind to surface antigens on the bacteria. In contrast, pre-incubation with PBS or the 741 antigen alone has no effect on the bactericidal activity of immune sera.

The competitive SBA results validate the SBA results for the 936 antigen described above and further support the conclusion that the 936 accessory protein is immunogenic against N. gonorrhoeae.

Example 7—High Bactericidal Titres are Maintained when BEXSERO® is Combined with MenACWY Antigens Female New Zealand rabbits (6 animals/group) were immunized with human dose of BEXSERO® alone or BEXSERO®+MenACWY (referred to as MenABCWY) in combination with an alum adjuvant intramuscularly on day 1, and 22. Sera samples were collected two weeks after the second dose and used for serological analysis.

Bactericidal Activity

Gonococcus strain FA1090 was grown in GC medium supplemented with 1% isovitalex for 1.5 hrs from $O.D._{600} \cong 0.1$ up to $O.D._{600} \cong 0.3$. The bacteria were diluted with a suspension of sera in SBA buffer (dPBS, 0.1% glucose, 1% BSA) and incubated for 1 hr at 37° C. with sera to be tested in the presence of human serum as exogenous complement source (16% v/v). Bacteria were then plated on a GC+1% isovitalex-plate.

Colonies were counted after 18 hrs of growth at 37° C. in 5% $CO_2$.

Serum bactericidal titers were calculated as the reciprocal dilution resulting in 50% killing with respect to the control (bacteria plus complement).

Results

Figure 14:
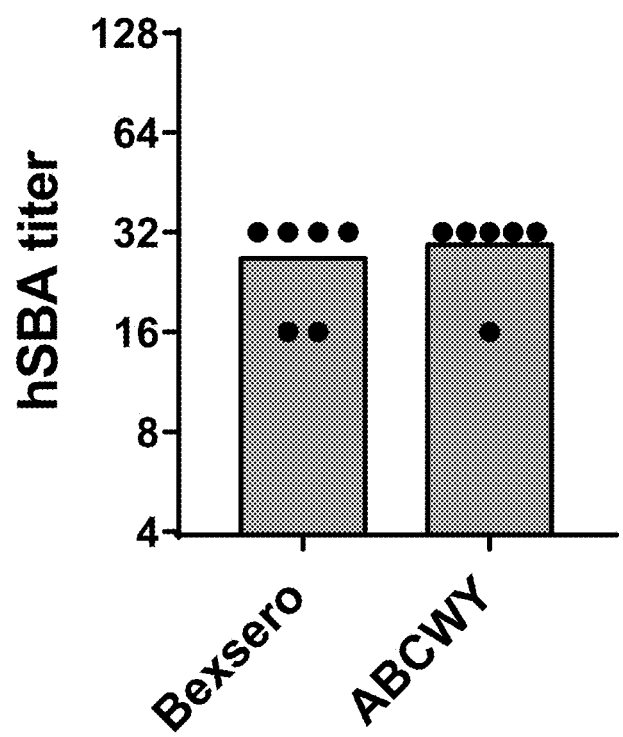
FIG. 14—Graph for hSBA results for BEXSERO® and MenABCWY shows that both compositions induce bactericidal antibodies against *N. gonorrhoeae* FA1090 strain.

As can be seen from FIG. 14, comparable results are seen in the hSBA assay for both anti-BEXSERO® and anti-MenABCWY sera. Both vaccines yield high SBA titres (16-32), indicating a strong bactericidal antibody response against N. gonorrhoeae. Each dot in the graph represents the result for immune serum from an individual rabbit, and these data show that both vaccines are able to induce a homogenous bactericidal response against N. gonorrhoeae, with the majority of the individual results producing a SBA titre of 32.

Example 8—dOMV from FA1090 Induces a Strong and Specific Bactericidal Antibody Response Against Homologous Strain Six-week-old female CD1 mice were immunized with 10 sg of OMV obtained from N. gonorrhoeae FA1090 strain in combination with an alum adjuvant intraperitoneally on day 1, 21 and 35. Protein F from Respiratory Syncytial Virus (RSV) was used as negative control. Sera samples were collected before the first immunization and two weeks after the last dose and used for serological analysis.

Bactericidal Activity

Gonococcus strain FA1090 was grown in GC medium supplemented with 1% isovitalex for 1.5 hrs from $O.D._{600} \cong 0.1$ up to $O.D._{600} \cong 0.3$. The bacteria were diluted with a suspension of sera in SBA buffer (dPBS, 0.1% glucose, 1% BSA) and incubated for 1 hr at 37° C. with sera to be tested in the presence of human serum as exogenous complement source (16% v/v). Bacteria were then plated on a GC+1% isovitalex-plate.

Colonies were Counted after 18 Hrs of Growth at 37° C. in 5% $CO_2$.

Serum bactericidal titers were calculated as the reciprocal dilution resulting in 50% killing with respect to the control (bacteria plus complement).

Results

Figure 15:
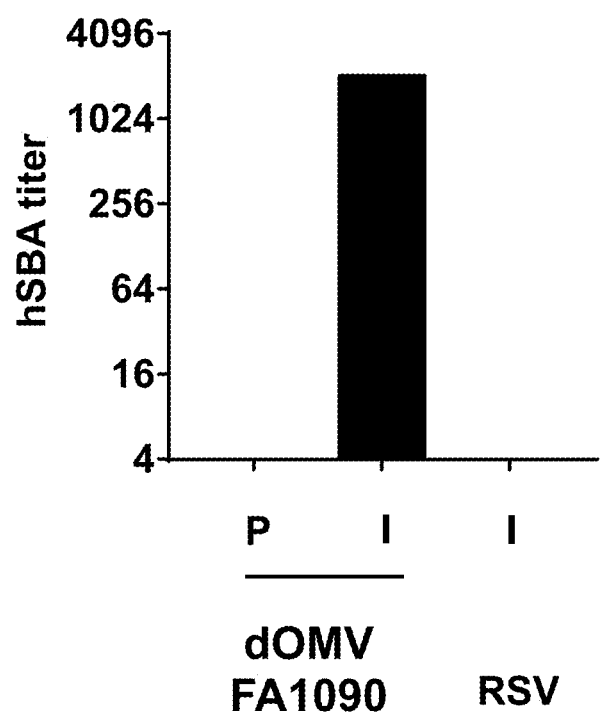
FIG. 15—Graph showing dOMV from *N. gonorrhoeae* FA1090 induces antibody response with strong SBA activity, inducing bactericidal antibodies against homologous strain.

As can be seen from FIG. 15, no hSBA result was observed for pre-immune serum (i.e. serum collected from the mice prior to immunization with dOMV FA1090) or the RSV immune serum. In contrast, the hSBA titres using immune serum from mice immunized with dOMV FA1090 (i.e. serum collected from the mice following immunization) was positive and produced an extremely high titre of ≥1024.

Competitive hSBA

The results observed in the SBA assays were reinforced by carrying out a competitive SBA assay to provide further indirect evidence of the immunogenic activity of gonococcal OMV against N. gonorrhoeae.

Figure 16:
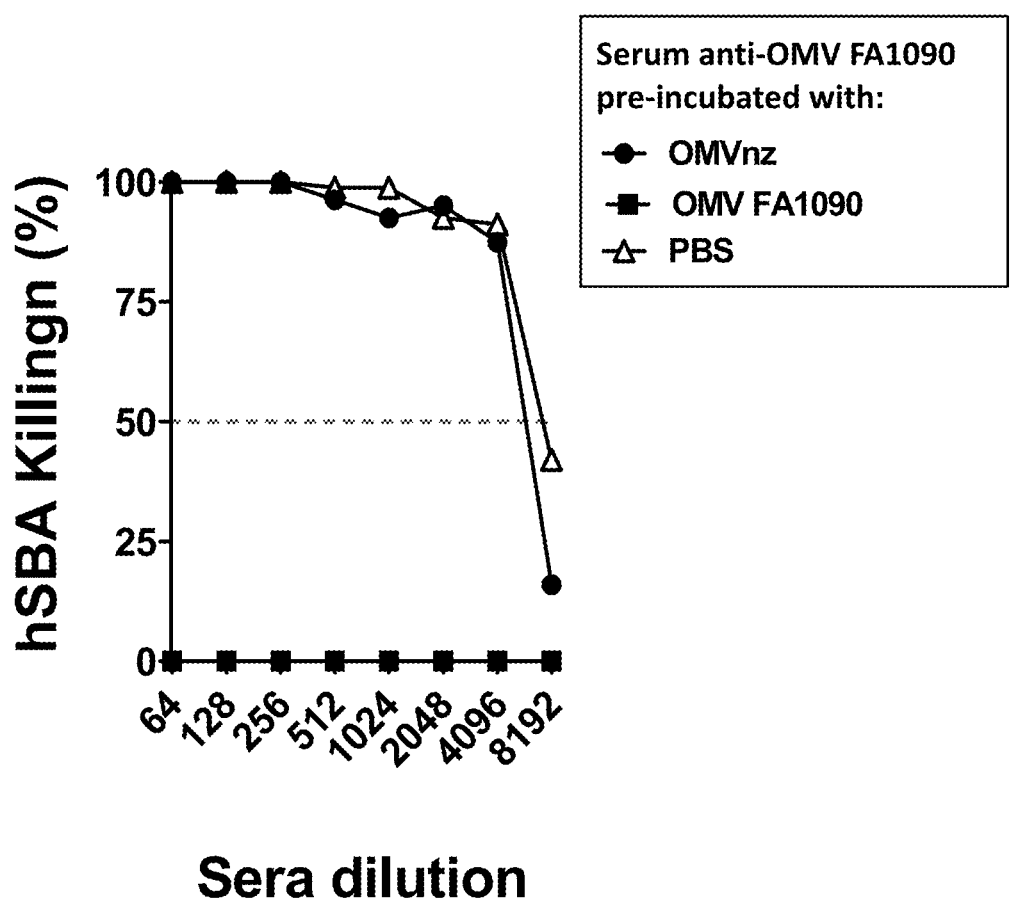
FIG. 16—Competitive hSBA showing that OMV FA1090 induces bactericidal antibodies, and confirming that the SBA activity of anti-OMV FA1090 serum is specific.

Sera from recipients who had been immunized with OMV FA1090 were pre-incubated with either (i) PBS (phosphate-buffered saline) as a negative control, or (ii) OMV FA1090. The sera were subsequently incubated with target gonococci bacteria in the presence of human complement. Killing of the bacteria was then assessed, and the results are shown in FIG. 16.

As can be seen in the graph, killing was abolished when the anti-OMV FA1090 immune sera was pre-incubated with OMV FA1090, because bactericidal antibodies in the recipients' sera bind to the antigens in these compositions during the pre-incubation phase and are therefore not available to bind to surface antigens on the bacteria. In contrast, pre-incubation with PBS had no effect on the bactericidal activity of immune sera.

The competitive hSBA results validate the SBA results for OMV FA1090 described above and provide further evidence that gonococcal-derived OMV induce a strong and specific bactericidal antibody response against N. gonorrhoeae.

Example 9—BEXSERO® Vaccine Induces Cross-Reactive T-Cell Responses Against N. Gonorrhoeae with Th1 Profile T-Cell Reponses Experimental Protocol CD1 mice (5 animals/group) were vaccinated with either (i) a BEXSERO® (1:2.5 human dose corresponding to 20 µg for each the protein antigens and 10 µg for the OMV). (ii) OMVnz, (10 µg) (iii) OMVFA1090 (10 sg), or (iv) $Al(OH)_3$ adjuvant alone, at days 1, 22 and 36. Splenocytes were isolated 2 weeks after the final vaccination, plated at 1-2× $10^6$ cells/well in 96-well plates, and stimulated with (i) OMV from gonococcus FA1090 strain or (ii) OMV from Escherichia coli (as a negative control) at final concentration of 10 µg/ml at 37° C. for 16-18 hrs in presence of anti-CD28 and anti-CD49d (2 µg/ml each, BD Biosciences) co-stimulatory molecules. Brefeldin A (5 µg/ml) was added for the last 4 hrs.

The cells were then stained with Live/Dead Yellow (Invitrogen), fixed and permeabilized with Cytofix/Cytoperm (BD Biosciences), washed in Perm/Wash buffer (BD Biosciences), incubated with anti-CD16/CD32 Fc block (BD Biosciences) for 20 min at room temperature, and then stained with fluorochrome-conjugated mAbs: anti-CD3-BV605, anti-CD4BV510, anti-IFN-γ-BV785, anti-IL-2-PE-Cy5, anti-TNF-Alexa488, anti-CD44-V450, anti-CD8-PE-CF594, anti-IL-17 PE-Cy7 and anti-IL-4-PerCPef710 and anti-IL-13-PerCPef710, in Perm/vWash buffer 1×(BD Biosciences) for 20 min at room temperature. Finally, the samples were washed twice in Perm/Wash buffer and suspended in PBS. Samples were acquired on LSRII flow cytometer (BD Biosciences) and analysed using FlowJo software (TreeStar).

Results

Figure 17:
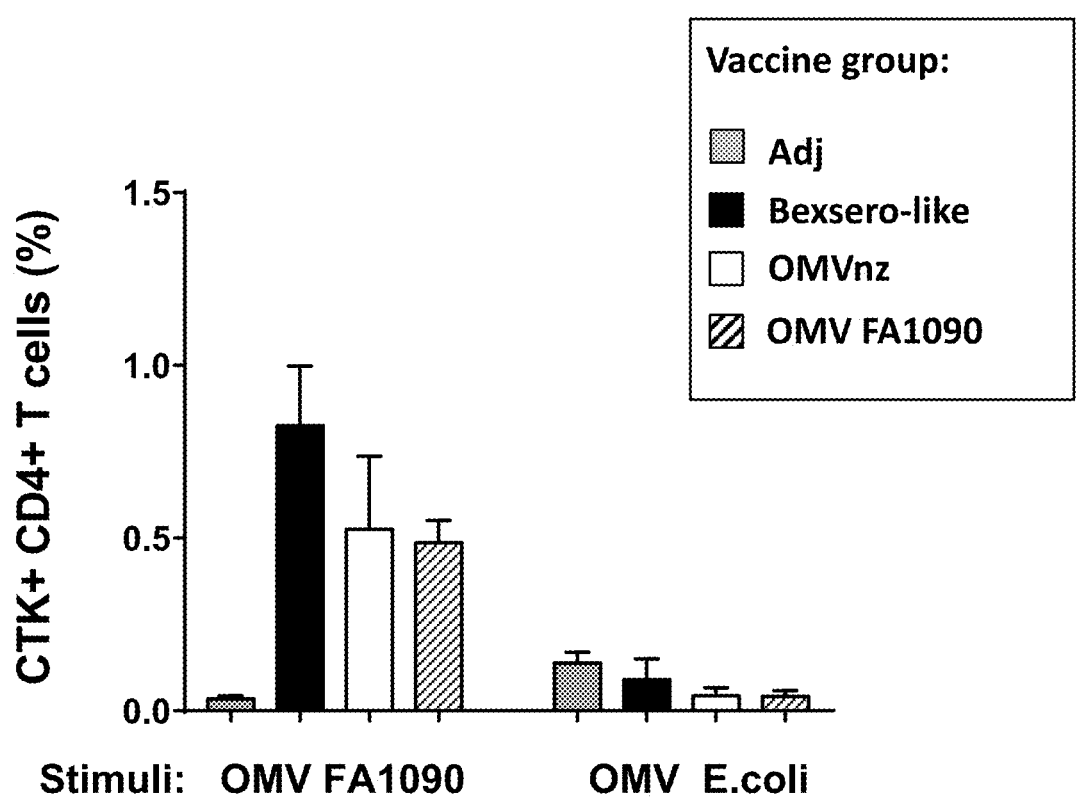
FIG. 17—Graph shows BEXSERO®, OMVnz and OMV FA1090 induce a CD4+ T-cell response against gonococcus strain FA1090.

As shown in FIG. 17, the BEXSERO® vaccine and the OMVnz vaccine were able to induce a cross-reactive CD4+ T-cells responses against gonococcal antigen OMV FA1090. The OMV FA1090-based vaccine was also able to induce a CD4+ T-cells responses against the homologous gonococcal antigen OMV FA1090. In contrast, none of these vaccines was unable to induce a T-cell response against the E. coli OMV antigen demonstrating that the T-cells responses is vaccine specific. Similarly, no significant CD4+ T-cell response was raised against either the gonococcus or E. coli OMV antigens in the population immunized with the adjuvant alone.

In order to understand the profile of the T-cells responses that was being raised, the inventors studied different cytokines produced by vaccine-specific CD4+ T-cells, which are known to be indicative of different T-cell response profiles, as follows:

TNF and IL-2 are associated with a Th0 profile.
IL-17 is associated with aTh17 profile.
IL-4 and IL-13 are associated with a Th2 profile.
IFN-γ is associated with aThI profile.

Figure 18E:
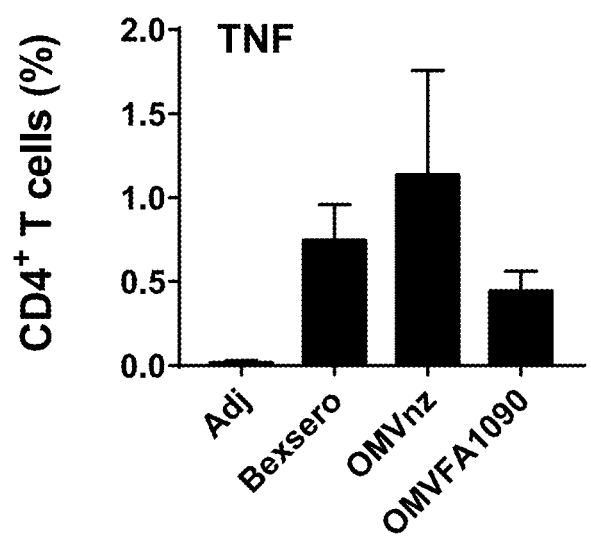

Comparison of the data in FIGS. 18 A-E indicates that the T-cell responses induced by the BEXSERO® vaccine against the gonococcal antigen exhibits a ThIFFhO profile, associated with the detection of IFN-γ (FIG. 18A) and TNF (FIG. 18E) respectively. This is an interesting result because the Th1 profile is thought to be associated with resistance to, and fast clearance of, gonococcus infection in the animal model.

Example 10—Human Monoclonal Antibody Derived from BEXSERO® Vaccination is Cross-Reactive and has Comparable Binding Affinity for Meningococcal and Gonococcal NHBA Proteins The inventors measured the association (Ka) and disassociation (Kd) constants of a human monoclonal antibody from human subjects vaccinated with BEXSERO® (HumAb 5H2) versus NHBA proteins from N. meningitidis and N. gonorrhoeae. This was done using commercially-available instrumentation from BIACORE®.

A BIACORE® microchip was loaded with an anti-human polyclonal antibody that captures the HumAb 5H2, then the NHBA proteins were immobilised on the microchip. The signal measured indicates the affinity (and stability) of the binding between the HumAb 5H2 and the two NHBA proteins.

Figure 19A:
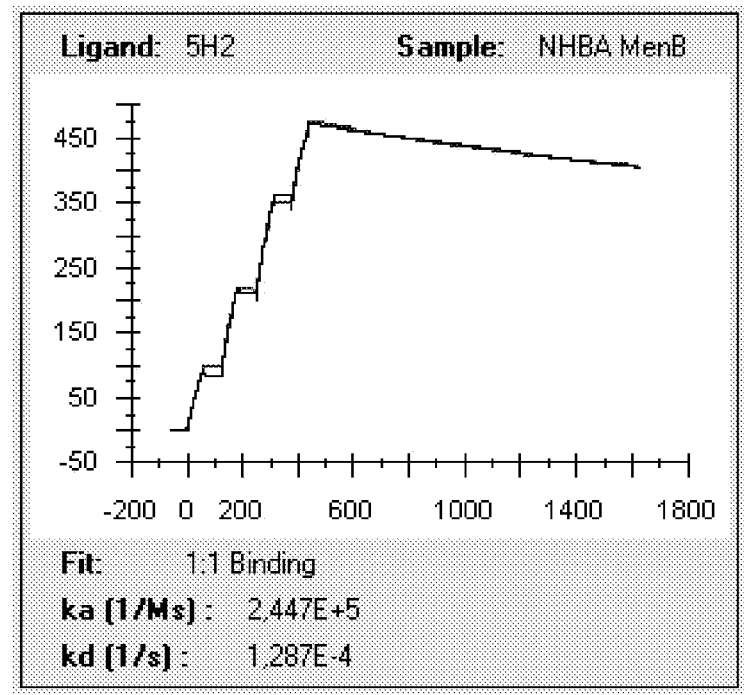
FIG. 19A-19B—Graphs show 5H2 ligand binding curve and Ka/Kd values for meningococcal NHBA (MenB) (FIG. 19A) and gonococcal NHBA (Ngo) (FIG. 19B).
Figure 19B:
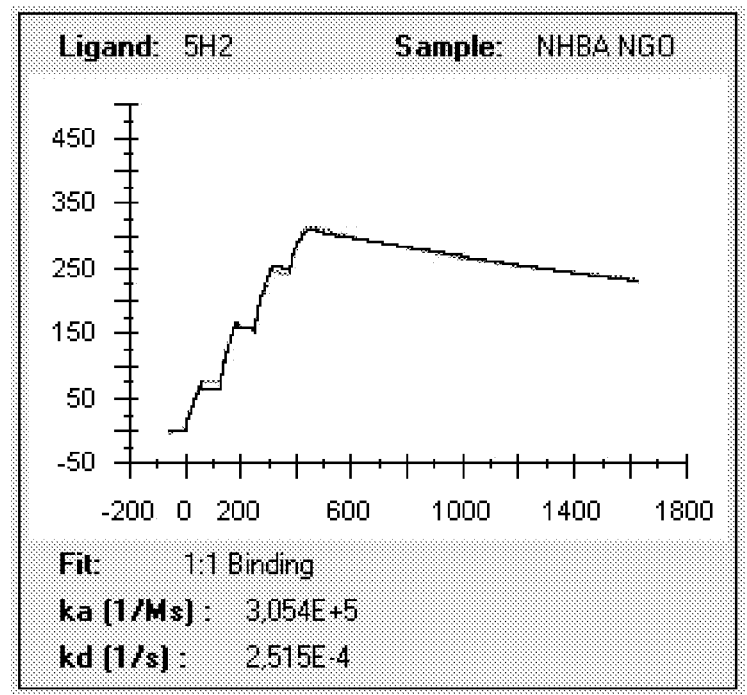

As shown in FIGS. 19A and 19B, the 5H2 ligand binding curve and Ka/Kd values are very similar for both NHBA MenB (FIG. 19A) and NHBA NG (FIG. 19B). These data show that there are common epitopes on the meningococcal and gonococcal NHBA proteins which are recognized by an antibody induced by immunization with BEXSERO®. In particular, the result shown in FIG. 19B demonstrates that an antibody induced by immunization with BEXSERO®, is cross-reactive and binds to gonococcal NHBA, which is expressed on the surface of N. gonorrhoeae. These data, considered in combination with other data presented in these Examples, support the utility of BEXSERO® as a vaccine against N. gonorrhoeae.

It will be understood that the invention is described above by way of example only and modifications may be made whilst remaining within the scope and spirit of the invention.

REFERENCES

[1] Newman et al. (2015) PloS one 10:c0143304.
[2] Lewis (2014) Curr. Opin. Infect. Dis. 27:62-67.
[3] Bolan et al. (2012) N. Engl. J. Med. 366:485-487.
[4] Mehta et al. (2003) Sexually transmitted infections 79:124-128.
[5] Edwards et al. (2016) Crit. Rev. Microbiol. 1-14.
[6] Zhu et al. (2011) Frontiers in Microbiology 2:124.
[7] Jerse et al. (2014) Vaccine 32:1579-1587.
[8] Jerse et al (2014) Vaccine 32:1579-87.
[9] Tinsley and Nassif (1996) Proc. Natl. Acad. Sci. USA 93:11109-11114.
[10] Muzzi et al (2013) mBio 4:e00163-13
[11] Bai et al. (2011) Expert Opin Biol Ther. 11:969-85.
[12] Su & Snape (2011) Expert Rev Vaccines 10:575-88.
[13] Gorringe & Pajon (2012) Human Vaccines & Immunotherapeutics 8:1-10.
[14] Giuliani et al. (2006) PNAS USA 103:10834-9.
[15] Regnier and Huels (2014) Hum. Vacc. Immunother. 10:3737-3745
[16] WO2005/102384.
[17] Jiang et al. (2010) Vaccine 28:6086-93.
[18] WO2013/186753
[19] Comanducci et al. (2002) J. Exp. Med. 195:1445-1454
[20] Hadad et al. (2012) APMIS 120:750-760.
[21] Jongerius 9(8):e1003528 (2013) PLoS Pathog. 9:e1003528
[22] Tettelin et al. (2000) Science 287:1809-1815.
[23] WO00/66741.
[24] WO99/57280
[25] Serruto et a. (2010) PNAS USA 107:3770-5.
[26] Comaducci et al. (2002) J Exp Med 195:1445-54.
[27] Masignani et al. (2003) J Exp Med 197:789-799.
[28] Welsch et al. (2004) J Immunol 172:5605-15.
[29] Hou et al. (2005) Infect Dis 192(4):580-90.
[ 30] WO03/063766.
[31] Fletcher et a. (2004) Infect Immun 72:2088-2100.
[32] Zhu et at (2005) Infect Immun 73(10):6838-45.
[33] Cantini et al. (2006) J. Biol Chem. 281:7220-7227
[34] Madico et a. (2006) J Immunol 177:501-10.
[35] WO2004/048404
[36] WO2009/104097.
[37] Rossi et al (2013) Vaccine 31:5451-7
[38] Parkhill et al. (2000) Nature 404:502-506.
[39] WO01/64920.
[40] WO01/64922.
[41] WO03/020756
[42] Beernink et al. (2009) J Infect Dis 199:1360-8.
[43] Pinto et al (2011) Vaccine 29:7752-8.
[44] WO02/09643.
[45] Katial et al. (2002) Infect. Immun. 70:702-707.
[46] U.S. Pat. No. 6,180,111.
[47] WO01/34642.
[48] WO2006/046143.
[49] WO2004/019977.
[50] European patent 0011243.
[51] Fredriksen et at (1991) NIPH Ann. 14(2):67-80.
[52] WO01/91788.
[53] WO2005/004908.
[54] WO2011/036562.
[55] Claassen et at (1996) Vaccine 14:1001-8.
[56] de Kleijn et al. (2000) Vaccine 18:1456-66.
[57] WO03/105890.
[58] WO2006/024946
[59] WO03/080678.
[60] Glode et al. (1979) J Infect Dis 139:52-56
[61] WO94/05325; U.S. Pat. No. 5,425,946.
[62] Arakere & Frasch (1991) Infect. Immun. 59:4349-4356.
[63] Michon et al. (2000) Dev. Biol 103:151-160.
[64] Rubinstein & Stein (1998) J. Immunol. 141:4357-4362.
[65] WO2005/033148
[66] WO02/058737
[67] WO2007/000314.

[68] *Vaccines.* (eds. Plotkin & Orenstein). 4th edition, 2004, ISBN: 0-7216-9688-0.
[69] U.S. Pat. No. 4,709,017.
[70] WO93/25210.
[71] U.S. Pat. No. 5,917,017.
[72] WO00/48638.
[73] Del Guidice et al. (1998) *Molecular Aspects of Medicine* 19:1-70.
[74] Anonymous (January 2002) *Research Disclosure,* 453077.
[75] Anderson (1983) *Infect Immun* 39(1):233-238.
[76] Anderson et al. (1985) *J Clin Invest* 76(1):52-59.
[77] EP-A-0372501.
[78] EP-A-0378881.
[79] EP-A-0427347.
[80] WO93/17712
[81] WO94/03208.
[82] WO98/58668.
[83] EP-A-0471177.
[84] WO91/01146
[85] Falugi et al. (2001) *Eur J Immunol* 31:3816-3824.
[86] Baraldo et al. (2004) Inject Immun 72(8):4884-7.
[87] EP-A-0594610.
[88] Ruan et al. (1990) *J Immunol* 145:3379-3384.
[89] WO00/56360.
[90] Kuo et al. (1995) *Infect Immun* 63:2706-13.
[91] Michon et al. (1998) *Vaccine.* 16:1732-41.
[92] WO02/091998.
[93] WO01/72337
[94] WO00/61761.
[95] WO00/33882
[96] WO99/42130
[97] U.S. Pat. No. 4,711,779.
[98] WO2007/000341.
[99] *Mol. Immunol.,* 1985, 22, 907-919
[100] EP-A-0208375
[101] Bethell et al. (1979). *J. Biol. Chem.,* 254, 2572-4
[102] Hearn (1981) *J. Chromatogr.,* 218:509-18
[103] WO00/10599
[104] Gever et al., *Med. Microbiol. Immunol,* 165: 171-288 (1979).
[105] U.S. Pat. No. 4,057,685.
[106] U.S. Pat. Nos. 4,673,574; 4,761,283; 4,808,700.
[107] U.S. Pat. No. 4,459,286.
[108] U.S. Pat. No. 5,204,098
[109] U.S. Pat. No. 4,965,338
[110] U.S. Pat. No. 4,663,160.
[111] WO2007/000343.
[112] U.S. Pat. No. 4,761,283
[113] U.S. Pat. No. 4,356,170
[114] WO2007/000342.
[115] Lees et al. (1996) *Vaccine* 14:190-198.
[116] WO95/08348.
[117] WO98/42721.
[118] WO03/007985
[119] *W.H.O. Tech. Rep. Ser.* 594:51, 1976.
[120] WO2007/000322.
[121] Gennaro (2000) *Remington: The Science and Practice of Pharmacy.* 20th edition. ISBN: 0683306472.
[122] *Vaccine Design* . . . (1995) eds. Powell & Newman. ISBN: 030644867X. Plenum.
[123] Loza et al. (2010) *Int. J. STD AIDS* 21:460-465
[124] *Methods In Enzymology* (S. Colowick and N. Kaplan, eds., Academic Press, Inc.)
[125] *Handbook of Experimental Immunology,* Vols. 1-IV (D. M. Weir and C. C. Blackwell, eds, 1986, Blackwell Scientific Publications)
[126] Sambrook et al. (2001) *Molecular Cloning: A Laboratory Manual.* 3rd edition (Cold Spring Harbor Laboratory Press).
[127] *Handbook of Surface and Colloidal Chemistry* (Birdi. K. S. ed., CRC Press, 1997)
[128] Ausubel et al. (eds) (2002) *Short protocols in molecular biology,* 5th edition (Current Protocols).
[129] *Molecular Biology Techniques: An Intensive Laboratory Course,* (Ream et al, eds., 1998, Academic Press)
[130] *PCR (Introduction to Biotechniques Series).* 2nd ed. (Newton & Graham eds., 1997. Springer Verlag)
[131] Gevsen et al. (1984) *PNAS USA* 81:3998-4002.
[132] Carter (1994) *Methods Mol Biol* 36:207-23.
[133] Jameson, B A et al. 1988, *CABIOS* 4(1):181-186.
[134] Raddrizzani & Hammer (2000) *Brief Bioinform* 1(2): 179-89.
[135] Bublil et al. (2007) *Proteins* 68(1):294-304.
[136] De Lalla et al. (1999) *J. Immunol.* 163:1725-29.
[137] Kwok et al. (2001) *Trends Immunol* 22:583-88.
[138] Brusic et al. (1998) *Bioinformatics* 14(2):121-30
[139] Meister et al (1995) *Vaccine* 13(6):581-91.
[140] Roberts et al. (1996) *AIDS Res Hum Retroviruses* 12(7):593-610.
[141] Maksyutov & Zagrebelnaya (1993) *Comput Appl Biosci* 9(3):291-7.
[142] Feller & de la Cruz (1991) *Nature* 349(6311):720-1.
[143] Hopp (1993) *Peptide Research* 6:183-190.
[144] Welling et al. (1985) *FEBS Lett.* 188:215-218.
[145] Davenport et al. (1995) *Immunogenetics* 42:392-297.
[146] Tsurui & Takahashi (2007) *J Pharmacol Sci.* 105(4): 299-316.
[147] Tong et al. (2007) *Brief Bioinform.* 8(2):96-108.
[148] Schirle et al. (2001) *J Immunol Methods.* 257(1-2):1-16.
[149] Chen et al. (2007) *Amino Acids* 33(3):423-8.
[150] *Current Protocols in Molecular Biology* (F. M. Ausubel et al., eds., 1987) Supplement 30
[151] Smith & Waterman (1981) *Adv. Appl. Math.* 2: 482489.

The invention claimed is:

1. A method of immunizing a human subject against *Neisseria gonorrhoeae* by administering to the subject a single dose or multiple doses of an immunogenic composition comprising an immunologically effective amount of a purified Neisserial Heparin Binding Antigen (NHBA) of *Neisseria meningitidis* comprising the amino acid sequence of SEQ ID NO: 8;
   wherein the human subject has been immunized against *N. meningitidis* during childhood;
   wherein the human subject who is immunized with the single dose or the multiple doses of the immunogenic composition is an adult at increased risk of infection with *N. gonorrhoeae* relative to the average risk in the general population; and
   wherein the immunogenic composition immunizes the human subject against infection or disease caused by *N. gonorrhoeae*.

2. The method of claim 1, wherein said immunogenic composition further comprises an immunologically effective amount of at least one meningococcal capsular saccharide antigen selected from meningococcal serogroups A, C, W135 and Y, wherein said capsular saccharide antigen is conjugated to a carrier protein.

3. The method of claim 1 where said immunogenic composition further comprises an immune enhancing amount of an adjuvant.

4. The method of claim 3 where said adjuvant is an aluminium salt adjuvant.

5. The method of claim 1, wherein the immunogenic composition further comprises a purified meningococcal NadA antigen comprising an amino acid sequence at least 95% identical to SEQ ID NO: 10; and a purified meningococcal fHbp antigen comprising an amino acid sequence at least 95% identical to SEQ ID NO: 6.

6. The method of claim 1, wherein said meningococcal NHBA is an NHBA-GNA1030 fusion protein, said fusion protein comprising the amino acid sequence of SEQ ID NO: 9.

7. The method of claim 5, wherein the meningococcal fHbp antigen comprises the amino acid sequence of SEQ ID NO: 6; the meningococcal NHBA antigen comprises the amino acid sequence of SEQ ID NO: 8; and the meningococcal NadA antigen comprises the amino acid sequence of SEQ ID NO: 10.

8. The method of claim 1, wherein the adult human subject is seropositive for *N. gonorrhoeae*.

9. The method of claim 1, wherein the childhood corresponds to an age of before 12 years.

10. The method of claim 9, wherein the adult is 18 years of age or older.

* * * * *